(12) United States Patent
Herr et al.

(10) Patent No.: US 10,588,759 B2
(45) Date of Patent: Mar. 17, 2020

(54) ARTIFICIAL HUMAN LIMBS AND JOINTS EMPLOYING ACTUATORS, SPRINGS AND VARIABLE-DAMPER ELEMENTS

(71) Applicant: Massachusetts Institute of Technology, Cambridge, MA (US)

(72) Inventors: Hugh M. Herr, Somerville, MA (US); Daniel Joseph Paluska, Silverthorne, CO (US); Peter Dilworth, Brighton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 26 days.

(21) Appl. No.: 15/098,725

(22) Filed: Apr. 14, 2016

(65) Prior Publication Data
US 2016/0228265 A1 Aug. 11, 2016

Related U.S. Application Data

(60) Division of application No. 13/171,307, filed on Jun. 28, 2011, now Pat. No. 9,333,097, which is a
(Continued)

(51) Int. Cl.
*A61F 2/64* (2006.01)
*A61F 2/68* (2006.01)
(Continued)

(52) U.S. Cl.
CPC ............. *A61F 2/604* (2013.01); *A61F 2/60* (2013.01); *A61F 2/64* (2013.01); *A61F 2/6607* (2013.01);
(Continued)

(58) Field of Classification Search
CPC .. A61F 2/64; A61F 2/68; A61F 2/6607; A61F 2002/5072; A61F 2002/6845; A61F 2/605
See application file for complete search history.

(56) References Cited

U.S. PATENT DOCUMENTS 2,489,291 A 11/1949 Henschke et al.
2,529,968 A 11/1950 Sartin
(Continued)

FOREIGN PATENT DOCUMENTS

CN 101061984 A 10/2007
CN 101111211 A 1/2008
(Continued)

OTHER PUBLICATIONS

Abbas, J.J. et al., "Neural Network Control of Functional Neuromuscular Stimulation Systems: Computer Simulation Studies," *IEEE Transactions on Biomedical Engineering*, vol. 42, No. 11, pp. 1117-1127, Nov. 1995.
(Continued)

*Primary Examiner* — Bruce E Snow
(74) *Attorney, Agent, or Firm* — Hamilton, Brook, Smith & Reynolds, P.C.

(57) ABSTRACT

It is to be understood that the methods and apparatus which have been described above are merely illustrative applications of the principles of the invention. Numerous modifications may be made by those skilled in the art without departing from the true spirit and scope of the invention.

15 Claims, 19 Drawing Sheets

Related U.S. Application Data continuation of application No. 11/395,448, filed on Mar. 31, 2006, now abandoned.

(60) Provisional application No. 60/704,517, filed on Aug. 1, 2005, provisional application No. 60/666,876, filed on Mar. 31, 2005.

(51) Int. Cl.

| | |
|---|---|
| *A61F 2/60* | (2006.01) |
| *A61F 2/66* | (2006.01) |
| *B25J 19/00* | (2006.01) |
| *B62D 57/032* | (2006.01) |
| *A61F 2/70* | (2006.01) |
| *A61F 2/50* | (2006.01) |
| *A61F 2/76* | (2006.01) |

(52) U.S. Cl.
 CPC ............... *A61F 2/68* (2013.01); *A61F 2/70* (2013.01); *B25J 19/0008* (2013.01); *B62D 57/032* (2013.01); *A61F 2/605* (2013.01); *A61F 2002/503* (2013.01); *A61F 2002/5004* (2013.01); *A61F 2002/5033* (2013.01); *A61F 2002/5072* (2013.01); *A61F 2002/5075* (2013.01); *A61F 2002/6818* (2013.01); *A61F 2002/701* (2013.01); *A61F 2002/704* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | | |
|---|---|---|---|
| 3,016,760 A | 1/1962 | Wrighton et al. | |
| 3,098,645 A | 7/1963 | Owens | |
| 3,207,497 A | 9/1965 | Schoonover | |
| 3,449,769 A | 6/1969 | Mizen | |
| 3,844,279 A | 10/1974 | Konvalin | |
| 3,871,032 A | 3/1975 | Karas | |
| 3,916,450 A | 11/1975 | Minor | |
| 4,442,390 A | 4/1984 | Davis | |
| 4,463,291 A | 7/1984 | Usry | |
| 4,518,307 A | 5/1985 | Bloch | |
| 4,532,462 A | 7/1985 | Washbourn et al. | |
| 4,546,295 A | 10/1985 | Wickham et al. | |
| 4,546,296 A | 10/1985 | Washbourn et al. | |
| 4,546,297 A | 10/1985 | Washbourn et al. | |
| 4,546,298 A | 10/1985 | Wickham et al. | |
| 4,569,352 A | 2/1986 | Petrofsky et al. | |
| 4,600,357 A | 7/1986 | Coules | |
| 4,657,470 A | 4/1987 | Clarke et al. | |
| 4,843,921 A | 7/1989 | Kremer | |
| 4,865,376 A | 9/1989 | Leaver et al. | |
| 4,872,665 A | 10/1989 | Chareire | |
| 4,872,803 A | 10/1989 | Asakawa | |
| 4,909,535 A | 3/1990 | Clark et al. | |
| 4,921,293 A | 5/1990 | Ruoff et al. | |
| 4,921,393 A | 5/1990 | Andeen et al. | |
| 4,923,474 A | 5/1990 | Klasson et al. | |
| 4,923,475 A | 5/1990 | Gosthnian et al. | |
| 4,936,295 A | 6/1990 | Crane | |
| 4,964,402 A | 10/1990 | Grim et al. | |
| 4,989,161 A | 1/1991 | Oaki | |
| 5,012,591 A | 5/1991 | Asakawa | |
| 5,049,797 A | 9/1991 | Phillips | |
| 5,062,673 A | 11/1991 | Mimura | |
| 5,088,478 A | 2/1992 | Grim | |
| 5,092,902 A | 3/1992 | Adams et al. | |
| 5,112,296 A | 5/1992 | Beard et al. | |
| 5,174,168 A | 12/1992 | Takagi et al. | |
| 5,181,933 A | 1/1993 | Phillips | |
| 5,252,102 A | 10/1993 | Singer et al. | |
| 5,294,873 A | 3/1994 | Seraji | |
| RE34,661 E | 7/1994 | Grim | |
| 5,327,790 A | 7/1994 | Levin et al. | |
| 5,332,203 A * | 7/1994 | Gossman | F16F 13/26 248/550 |
| 5,367,790 A | 11/1994 | Gamow et al. | |
| 5,383,939 A | 1/1995 | James | |
| 5,405,409 A | 4/1995 | Knoth | |
| 5,442,270 A | 8/1995 | Tetsuaki | |
| 5,443,521 A | 8/1995 | Knoth et al. | |
| 5,456,341 A | 10/1995 | Garnjost et al. | |
| 5,458,143 A | 10/1995 | Herr | |
| 5,476,441 A | 12/1995 | Durfee et al. | |
| 5,502,363 A | 3/1996 | Tasch et al. | |
| 5,514,185 A | 5/1996 | Phillips | |
| 5,556,422 A | 9/1996 | Powell, III et al. | |
| 5,571,205 A | 11/1996 | James | |
| 5,643,332 A | 7/1997 | Stein | |
| 5,650,704 A * | 7/1997 | Pratt | B25J 9/10 318/560 |
| 5,662,693 A | 9/1997 | Johnson et al. | |
| 5,701,686 A | 12/1997 | Herr et al. | |
| 5,718,925 A | 2/1998 | Kristinsson et al. | |
| 5,748,845 A | 5/1998 | Labun et al. | |
| 5,776,205 A | 7/1998 | Phillips | |
| 5,865,770 A | 2/1999 | Schectman | |
| 5,885,809 A | 3/1999 | Effenberger et al. | |
| 5,888,212 A | 3/1999 | Petrofsky et al. | |
| 5,888,213 A | 3/1999 | Sears et al. | |
| 5,898,948 A | 5/1999 | Kelly et al. | |
| 5,910,720 A | 6/1999 | Williamson et al. | |
| 5,932,230 A | 8/1999 | DeGrate | |
| 5,944,760 A | 8/1999 | Christensen | |
| 5,971,729 A | 10/1999 | Kristinsson et al. | |
| 5,972,036 A | 10/1999 | Kristinsson et al. | |
| 5,980,435 A | 11/1999 | Joutras et al. | |
| 6,029,374 A | 2/2000 | Herr et al. | |
| 6,056,712 A | 5/2000 | Grim | |
| 6,067,892 A | 5/2000 | Erickson | |
| 6,071,313 A | 6/2000 | Phillips | |
| 6,136,039 A | 10/2000 | Kristinsson et al. | |
| 6,144,385 A | 11/2000 | Girard | |
| 6,202,806 B1 | 3/2001 | Sandrin et al. | |
| 6,223,648 B1 | 5/2001 | Erickson | |
| 6,240,797 B1 | 6/2001 | Morishima et al. | |
| 6,267,742 B1 | 7/2001 | Krivosha et al. | |
| 6,416,703 B1 | 7/2002 | Kristinsson et al. | |
| 6,443,993 B1 | 9/2002 | Koniuk | |
| 6,456,884 B1 | 9/2002 | Kenney | |
| 6,478,826 B1 | 11/2002 | Phillips et al. | |
| 6,485,776 B2 | 11/2002 | Janusson et al. | |
| 6,507,757 B1 | 1/2003 | Swain et al. | |
| 6,511,512 B2 | 1/2003 | Phillips et al. | |
| 6,517,503 B1 | 2/2003 | Naft et al. | |
| 6,532,400 B1 | 3/2003 | Jacobs | |
| 6,585,774 B2 | 7/2003 | Dean, Jr. et al. | |
| 6,589,289 B2 | 7/2003 | Ingimarsson | |
| 6,592,539 B1 | 7/2003 | Einarsson et al. | |
| 6,610,101 B2 | 8/2003 | Herr et al. | |
| 6,626,952 B2 | 9/2003 | Janusson et al. | |
| 6,660,042 B1 | 12/2003 | Curcie et al. | |
| 6,666,796 B1 | 12/2003 | MacCready, Jr. | |
| 6,706,364 B2 | 3/2004 | Janusson et al. | |
| 6,752,774 B2 | 6/2004 | Townsend et al. | |
| 6,764,520 B2 | 7/2004 | Deffenbaugh et al. | |
| 6,811,571 B1 | 11/2004 | Phillips | |
| D503,480 S | 3/2005 | Ingimundarson et al. | |
| D503,802 S | 4/2005 | Bjarnason | |
| 6,887,279 B2 | 5/2005 | Phillips et al. | |
| 6,923,834 B2 | 8/2005 | Karason | |
| 6,936,073 B2 | 8/2005 | Karason | |
| 6,942,629 B2 | 9/2005 | Hepburn et al. | |
| 6,945,947 B2 | 9/2005 | Ingimundarson et al. | |
| 6,966,882 B2 | 11/2005 | Horst | |
| 6,969,408 B2 | 11/2005 | Lecomte et al. | |
| 7,001,563 B2 | 2/2006 | Janusson et al. | |
| 7,025,793 B2 | 4/2006 | Egilsson | |
| 7,029,500 B2 | 4/2006 | Martin | |
| 7,037,283 B2 | 5/2006 | Karason et al. | |
| D523,149 S | 6/2006 | Bjarnason | |

(56) References Cited

U.S. PATENT DOCUMENTS

| | | |
|---|---|---|
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,314,490 B2 | 1/2008 | Bédard et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,485,152 B2 | 2/2009 | Haynes et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 * | 6/2010 | Bedard .......... A61F 2/644 623/24 |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |

(56) References Cited

U.S. PATENT DOCUMENTS

| | | |
|---|---|---|
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 | 8/2013 | Herr et al. |
| 8,734,528 B2 | 5/2014 | Herr et al. |
| 8,864,846 B2 | 10/2014 | Herr et al. |
| 8,870,967 B2 | 10/2014 | Herr et al. |
| 9,149,370 B2 | 10/2015 | Herr et al. |
| 9,221,177 B2 | 12/2015 | Herr et al. |
| 9,339,097 B2 | 5/2016 | Herr et al. |
| 9,339,397 B2 | 5/2016 | Herr et al. |
| 9,539,117 B2 | 1/2017 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0038525 A1 | 2/2005 | Doddroe et al. |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0192677 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2008/0169729 A1 | 7/2008 | Asai |
| 2009/0030530 A1 | 1/2009 | Martin |
| 2009/0222105 A1 | 9/2009 | Clausen |
| 2009/0265018 A1 | 10/2009 | Goldfarb et al. |
| 2010/0113988 A1 | 5/2010 | Matsuoka et al. |
| 2010/0241242 A1 | 9/2010 | Herr et al. |
| 2010/0256537 A1 | 10/2010 | Menga |
| 2010/0324699 A1 | 12/2010 | Herr et al. |
| 2011/0040216 A1 | 2/2011 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr |
| 2013/0310979 A1 | 11/2013 | Herr et al. |
| 2014/0046455 A1 | 2/2014 | Herr et al. |
| 2014/0088729 A1 | 3/2014 | Herr et al. |
| 2014/0257519 A1 | 9/2014 | Herr et al. |
| 2015/0051710 A1 | 2/2015 | Herr et al. |
| 2016/0207201 A1 | 7/2016 | Herr et al. |
| 2016/0338857 A1 | 11/2016 | Herr et al. |
| 2017/0049587 A1 | 2/2017 | Herr et al. |
| 2017/0349022 A1* | 12/2017 | Masamura ........... B60G 17/015 |

FOREIGN PATENT DOCUMENTS

| | | |
|---|---|---|
| EP | 1169982 | 1/2002 |
| EP | 1393866 | 3/2004 |
| JP | 2008-87143 A | 4/2008 |
| WO | WO 2001/054630 A1 | 8/2001 |
| WO | WO 2003/005934 A2 | 1/2003 |
| WO | WO 2003/068453 | 8/2003 |
| WO | WO 2004/017872 A1 | 3/2004 |
| WO | WO 2004/019832 A1 | 3/2004 |
| WO | WO 2010/027968 A2 | 3/2010 |
| WO | WO 2010/088616 | 8/2010 |
| WO | WO 2010/088635 A1 | 8/2010 |

OTHER PUBLICATIONS

Abul-Haj, C.J. et al., "Functional Assessment of Control Systems for Cybernetic Elbow Prostheses-Part II: Application of the Technique," *IEEE Transactions on Biomedical Engineering*, vol. 17, No. 11, pp. 1037-1047, Nov. 1990.

Aeyels, B., et al., "An EMG-Based Finite State Approach for a Microcomputer-Controlled Above-Knee Prosthesis," Engineering in Medicine and Biology Society 1995, pp. 1315-1316 (1997).

Akazawa, K. et al., "Biomimetic EMG-Prosthesis-Hand, 18th Annual International Conference of the IEEE Engineering in Medicine and Biology Society," Amsterdam pp. 535 and 536, 1996.

Aminian, K. et al., "Estimation of Speed and Incline of Walking Using Neural Network," *IEEE Transactions of Instrumentation and Measurement*, 44(3): 743-746 (1995).

Anderson, F.C. et al., "Dynamic Optimization of Human Walking," *Journal of Biomechanical Engineering*, 123: 381-390 (2001).

Andrews, B.J. et al., "Hybrid FES Orthosis Incorporating Closed Loop Control and Sensory Feedback," *J. Biomed. Eng.*, 10: 189-195(1988).

(56) References Cited

OTHER PUBLICATIONS

Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.

Au, et al., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, et al., "Powered Ankle-Foot Prosthesis: The Importance of Series and Parallel Motor Elasticity," IEEE Robotics & Automation Magazine, pp. 52-59, Sep. 2008.

Au, S. et al., "Powered Ankle-Foot Prosthesis to Assist Level-Ground and Stair-Descent Gaits," Neural Networks, 21: 654-666 (2008).

Au, S.K. et al., "An Ankle-Foot Emulation System for the Study of Human Walking Biomechanics," Proceedings of the 2006 IEEE International Conference on Robotics and Automation, Orlando, FL, May 2006, pp. 2939-2945.

Au, S.K. et al., "An EMG-Position Controlled System for an Active Ankle-Foot Prosthesis: An Initial Experimental Study," Proceedings of the 2005 IEEE $9^{th}$ International Conference on Rehabilitation Robotics, Chicago, IL., pp. 375-379.

Au, S.K. et al., "Biomechanical Design of a Powered Ankle-Foot Prosthesis," Proceedings of the 2007 IEEE $10^{th}$ International Conference on Rehabilitation Robotics, Noordwijk, The Netherlands, pp. 298-303, Jun. 12-15, 2007.

Au, S.K. et al., "Powered Ankle-Foot Prosthesis for the Improvement of Amputee Ambulation," paper presented at the Proceedings of the $29^{th}$ Annual International Conference of the IEEE Eng. Med. Bio. Soc., Cité Internationale, Lyon, France, (Aug. 2007).

Au, S.K. et al., "Powered Ankle-Foot Prosthesis Improves Walking Metabolic Economy," IEEE Transactions on Robotics, 25(1): 51-66 (2009).

Barth, D.G. et al., "Gait Analysis and Energy Cost of Below-Knee Amputees Wearing Six Different Prosthetic Feet," JPO, 4(2): 63 (1992).

Baten, Chris T.M. et al., "Inertial Sensing in Ambulatory Back Load Estimation," paper presented at the $18^{th}$ Annual International Conference of the IEEE Engineering in Medicine and Biology Society, Amsterdam, 1996, pp. 497-498.

Bateni, H. et al., "Kinematic and Kinetic Variations of Below-Knee Amputee Gait," JPO, 14(1):1-12 (2002).

Blaya, J. et al., "Active Ankle Foot Orthoses (AAFO)," Artificial Intelligence Laboratory, Massachusetts Institute of Technology, Cambridge, MA, pp. 275-277. (no date given).

Blaya, J.A. et al., "Active Ankle Foot Orthoses (AAFO)," Retrieved from: http://www.ai.mit.edu. Artificial Intelligence Laboratory, Massachusetts Institute of Technology, Cambridge, Massachusetts, pp. 251-253 (no date given).

Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages, no date given.

Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blickhan, R., "The Spring-Mass Model for Running and Hopping," J. Biomechanics, 22(11 /12): 1217-1227 (1989).

Bortz, J.E. "A New Mathematical Formulation for Strapdown Inertial Navigation," IEEE Transactions on Aerospace and Electronic Systems, AES-7(1): 61-66 (1971).

Bouten, C.V. et al., "Assessment of Energy Expenditure for Physical Activity Using a Triaxial Accelerometer," Medicine and Science in Sports and Exercise, 26(12): 1516-1523 (1994).

Brockway, J.M., "Derivation of Formulae Used to Calculate Energy Expenditure in Man," Human Nutrition: Clinical Nutrition 41C, pp. 463-471 (1987).

Brown, T.G., "On the Nature of the Fundamental Activity of the Nervous Centres; Together with an Analysis of the Conditioning of Rhythmic Activity in Progression, and a Theory of the Evolution of Function in the Nervous System," pp. 24-46 (no date given).

Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.

Colborne, G.R., et al., "Analysis of mechanical and metabolic factors in the gait of congenital below knee amputees," Am. J. Phys. Med. Rehabil., vol. 92, pp. 272-278, Oct. 1992.

Colgate, J.E., "The Control of Dynamically Interacting Systems," Massachusetts Institute of Technology, pp. 1-15, Aug. 1988.

Collins, S.H. et al., "Controlled Energy Storage and Return Prosthesis Reduces Metabolic Cost of Walking," ISB XXth Congress-ASB $29^{th}$ Annual Meeting, Jul. 31-Aug. 5, Cleveland, Ohio, pp. 804 (no year given).

Collins, S.H., et al., "A Bipedal Walking Robot with Efficient and Human-Like Gait," 2005 IEEE, Int'l Conference on Robotics and Automation, Barcelona, Spain, pp. 1983-1988, (Apr. 2005).

Collins, S.H., et al., Supporting Online Material for "Efficient Bipedal Robots Based on Passive-Dynamic Walkers," Mechanical Engineering, University of Michigan, Feb. 11, 2005, Ann Arbor, MI, pp. 1-8.

Crago, P.E. et al., "New Control Strategies for Neuroprosthetic Systems," Journal of Rehabilitation Research and Development, vol. 33, No. 2, Apr. 1996, pp. 158-172.

Daley, M.A. et al. , "Running Stability is Enhanced by a Proximo-Distal Gradient in Joint Neuromechanical Control," The Journal of Experimental Biology, vol. 210, pp. 383-394 (Feb. 2007).

Dapena, J. et al., " A Three-Dimensional Analysis of Angular Momentum in the Hammer Throw," Biomechanics Laboratory, Indiana University, IN, Medicine and Science in Sports and Exercise, vol. 21, No. 2, pp. 206-220 (1988).

Davids, J.R., "Book Reviews" Journal of Pediatric Orthopedics 12, pp. 815, 1992.

Dietz, V. "Proprioception and Locomotor Disorders," Nature Reviews, vol. 3, pp. 781-790 (Oct. 2002).

Dietz, V. "Spinal Cord Pattern Generators for Locomotion," Clinical Neurophysiology, vol. 114, Issue 8, pp. 1-12 (Aug. 2003).

Doerschuk, P.C. et al., "Upper Extremity Limb Function Discrimination Using EMG Signal Analysis," IEEE Transactions on Biomedical Engineering, vol. BME-30, No. 1, Jan. 1983, pp. 18-28.

Doke, J. et al., "Mechanics and Energetics of Swinging the Human Leg," The Journal of Experimental Biology, vol. 208, pp. 439-445 (2005).

Dollar, A.M. et al., "Lower Extremity Exoskeletons and Active Orthoses: Challenges and State-of-the-Art," IEEE Transactions on Robotics, vol. 24, No. 1, pp. 1-15, Feb. 2008.

Donelan, J.M. et al., "Force Regulation of Ankle Extensor Muscle Activity in Freely Walking Cats," Journal of Neurophysiology, vol. 101, pp. 360-371 (2009).

Donelan, J.M. et al., "Mechanical work for Step-to-Step Transitions is a Major Determinant of the Metabolic Cost of Human Walking," The Journal of Experimental Biology, vol. 205, pp. 3717-3727 (2002).

Donelan, J.M. et al., "Simultaneous Positive and Negative External Mechanical Work in Human Walking," Journal of Biomechanics, vol. 35, 2002, pp. 117-124 (2002).

Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.

Drake, C., "Ankle & Foot Splints or Orthoses (AFOs)," HemiHelp Information Sheet, pp. 1-6, last revision Dec. 2011.

Drake, C., "Foot & Ankle Splints or Orthoses," HemiHelp Information Sheet No. 13, pp. 1-5, last update Jun. 2009.

(56) References Cited

OTHER PUBLICATIONS

Eilenberg, et al., "Control of a Powered Ankle-Foot Prosthesis Based on a Neuromuscular Model," *IEEE Transactions on Neural Systems & Rehabilitation Eng.*, vol. 18(2):164-173 (2010).
Eilenberg, M.F. "A Neuromuscular-Model Based Control Strategy for Powered Ankle-Foot Prostheses," Massachusetts Institute of Technology, pp. 1-90. Jul. 20, 2010.
Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).
Ekeberg, Ö et al., "Simulations of Neuromuscular Control in Lamprey Swimming," The Royal Society, *Phil. Trans. R. Soc. Land*, vol. 354, pp. 895-902 (1999).
Endo, K. et al., "A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.
Eppinger, S.D. et al., "Three Dynamic Problems in Robot Force Control," *IEEE Transactions on Robotics and Automation*, vol. 8, No. 6, pp. 772-778 (Dec. 1992).
Esquenazi, M.D., A., et al., "Rehabilitation After Amputation," *J Am Podiatr Med Assoc* vol. 91, No. 1, pp. 13-22 (Jan. 2001).
Farley, C.T. et al., "Energetics of Walking and Running: Insights From Simulated Reduced-Gravity Experiments," *J. Appl. Physiol.* 73(6):2709-2712 (1992).
Farry, K.A. et al., "Myoelectric Teleoperation of a Complex Robotic Hand," *IEEE Transactions on Robotics and Automation*, vol. 12, No. 5, pp. 775-778 (Oct. 1996).
Featherstone, R., "Robot Dynamics Algorithms," Edinburgh University, pp. 1-173, 1987.
Fite, K. et al., "Design and Control of an Electrically Powered Knee Prosthesis," Proceedings of the 2007 IEEE 10$^{th}$ International Conference on Rehabilitation Robotics, Jun. 12-15, The Netherlands, pp. 902-905.
Flowers, W.C., "A Man-Interactive Simulator System for Above-Knee Prosthetics Studies," Partial fulfillment for Doctor of Philosophy, MIT, pp. 1-94 Aug. 1972.
Fod, A. et al., "Automated Derivation of Primitives for Movement Classification," *Autonomous Robots*, vol. 12, No. 1, pp. 39-54 (Jan. 2002).
Frigon, A. et al., "Experiments and Models of Sensorimotor Interactions During Locomotion," *Biological Cybernetics*, vol. 95, pp. 606-627 (2006).
Fujita et al., "Joint Angle Control with Command Filter for Human Ankle Movement Using Functional Electrical Stimulation," Proceedings of the Ninth Annual Conference of the IEEE Engineering in Medicine and Biology Society, Boston, MA, Nov. 13-16, 1987.
Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).
Gates, D.H. Thesis: "Characterizing Ankle Function During Stair Ascent, Descent, and Level Walking for Ankle Prosthesis and Orthosis Design," Boston University, pp. 1-84 (2004).
Gerritsen, K.G.M. et al., "Direct Dynamics Simulation of the Impact Phase in Heel-Toe Running," *J. Biomechanics*, vol. 28, No. 6, pp. 661-668 (1995).
Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).
Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10 (2010).
Geyer, H. et al., "Compliant Leg Behavior Explains Basic Dynamics of Walking and Running," *Proc. R. Soc. B*, vol. 273, pp. 2861-2867 (2006).
Geyer, H. et al., "Positive Force Feedback in Bouncing Gaits?," *Proc. R. Soc. Lond, B*, vol. 270, pp. 2173-2183 (2003).
Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).
Giszter, S., et al., "Convergent Force Fields Organized in the Frog's Spinal Cord," *Journal of Neuroscience*, 13(2): 467-491 (1993).
Godha, S. et al., "Integrated GPS/INS System for Pedestrian Navigation in a Signal Degraded Environment," ION GNSS, Fort Worth, TX, Sep. 26-29, 2006 pp. 1-14.
Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.
Goswami, A., "Postural Stability of Biped Robots and the Foot-Rotation Indicator (FRI) Point" *The International Journal of Robotics Research*, vol. 18, No. 6, pp. 523-533 (Jun. 1999).
Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).
Gregoire, L. et al., "Role of Mono- and Biarticular Muscles in Explosive Movements," *International Journal of Sports Medicine*, vol. 5, No. 6, pp. 299-352 (Dec. 1984).
Grillner, S. and Zangger, P., "On the Central Generation of Locomotion in the Low Spinal Cat," *Experimental Brain Research*, 34: 241-261 (1979).
Grimes, D.L., "An Active Multi-Mode Above-Knee Prosthesis Controller," unpublished doctoral dissertation, Massachusetts Institute of Technology (1979).
Gu, W.J., "The Regulation of Angular Momentum During Human Walking," unpublished doctoral dissertation, Massachusetts Institute of Technology, 42 pages (2003).
Gunther, M. et al., "Human Leg Design: Optimal Axial Alignment Under Constraints," *J. Math. Biol.*, 48: 623-646 (2004).
Günther, M., and Ruder, H., "Synthesis of Two-Dimensional Human Walking: a test of the λ-model," *Biol. Cybern.*, 89: 89-106 (2003).
Hanafusa, et al., "A Robot Hand with Elastic Fingers and Its Application to Assembly Process," pp. 337-359, Robot Motion, Brady, et al., MIT Press, Cambridge, MA 1982.
Hansen, A.H., et al., "The Human Ankle During Walking: Implications for Design of Biomimetic Ankle Prostheses," *Journal of Biomechanics*, 37: 1467-1474 (2004).
Hayes, W.C., et al., "Leg Motion Analysis During Gait by Multiaxial Accelerometry: Theoretical Foundations and Preliminary Validations," *Journal of Biomechanical Engineering*, 105: 283-289 (1983).
Heglund, N. et al., "A Simple Design for a Force-Plate to Measure Ground Reaction Forces," *J. Exp. Biol.*, 93: 333-338 (1981).
Herr, H.M. et al., "A Model of Scale Effects in mammalian Quadrupedal Running," *The Journal of Experimental Biology*, 205: 959-967 (2002).
Herr, H.M., and McMahon, T.A., "A Trotting Horse Model," *The International Journal of Robotics Research*, 19: 566-581 (2000).
Herr, H.M., and Popovic, M., "Angular Momentum in Human Walking," *The Journal of Experimental Biology*, 211: 467-481 (2008).
Herr, H.M., and Wilkenfeld, A., "User-adaptive Control of a Magnetorheological Prosthetic Knee," *Industrial Robot: An International Journal*, 30(1): 42-55 (2003).
Herr, Hugh et al. "New Horizons for Orthotic and Prosthetic Technology: Artificial Muscle for Ambulation," The MIT Media Laboratory, pp. 1-9, 2004.
Heyn, A., et al., "The Kinematics of the Swing Phase Obtained From Accelerometer and Gyroscope Measurements," paper presented at the 18$^{th}$ Annual International Conference of the IEEE Engineering in Medicine and Biology Society, Amsterdam (1996).
Hill, A.V., "The Heat of Shortening and the Dynamic Constants of Muscle," *Proc. R. Soc. Lond.*, 126: 136-195 (1938).
Hirai, K., et al., "The Development of Honda Humanoid Robot," paper presented at the IEEE International Conference on Robotics & Automation, Leuven, Belgium (1998).
Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Com-

(56) References Cited

OTHER PUBLICATIONS puters and Information in Engineering Conference, vol. 5 Part C, DETC2007-34512, pp. 1587-1596, Las Vegas, Nevada (Sep. 2007).
Hof, A.L., et al., "Calf Muscle Moment, Work and Efficiency in Level Walking: Role of Series Elasticity," *J. Biochem.*, 16: 523-537 (1983).
Hofbaur, M.W., and Williams, B.C., "Mode Estimation of Probabilistic Hybrid Systems," MIT Space Systems and Artificial Intelligence Laboratories and Graz University of Technology, Department of Automatic Control, (No Date given).
Hofbaur, M.W., et al., "Hybrid Diagnosis with Unknown Behavioral Modes," Proceedings of the 13$^{th}$ International Workshop on Principles of Diagnosis (DX02) (2002).
Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).
Hofmann, A.G., "Robust Execution of Bipedal Walking Tasks From Biomechanical Principles," unpublished doctoral dissertation for Massachusetts Institute of Technology (2006).
Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).
Hogan, N., "Impedance Control: An Approach to Manipulation: Part II—Implementation, " *Journal of Dynamic Systems, Measurement, and Control*, 107: 8-16 (1985).
Hogan, N., "A Review of the Methods of Processing EMG for Use as a Proportional Control Signal," *Biomedical Engineering*, 11(3): 81-86 (1976).
Hogan, N., "Impedance Control: An Approach to Manipulation: Part I—Theory," *Journal of Dynamic Systems, Measurement, and Control*, 107: 1-7 (1985).
Hogan, N., "Impedance Control: An Approach to Manipulation: Part III—Application," *Journal of Dynamics Systems, Measurement and Control*, 107: 17-24 (1985).
Hogan, N., and Buerger, S.P., "Impedance and Interaction Control, Robot and Automation Handbook, Chapter 19, ® 2005 by CRC Press LLC, 24 pgs."
Holgate, M.A., et al., "The SPARKy (Spring Ankle with Regenerative Kinetics) Project: Choosing a DC Motor Based Actuation Method," Proceedings of the 2nd Biennial IEEE-EMBS International Conf. on Biomedical Robotics and Biomechatronics, Scottsdale, AZ, pp. 163-168, Oct. 19-22, 2008.
Hollander, K.W. et al., "Adjustable Robotic Tendon using a 'Jack Spring'™," Proceedings of the 2005 IEEE, 9$^{th}$ International Conference on Rehabilitation Robotics, Jun. 28-Jul. 1, 2005, Chicago, IL, USA, pp. 113-118.
Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.
Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).
Huang, Q. et al., "Planning Walking Patterns for a Biped Robot," *IEEE Transactions on Robotics and Automation*,17(3): 280-289 (Jun. 2001).
Hultborn, H., "Spinal reflexes, mechanisms and concepts: From Eccles to Lundberg and beyond," *Progress in Neurobiology*,78: 215-232 (2006).
Ijspeert, A.J. et al., "From swimming to walking with a salamander robot driven by a spinal cord model," pp. 1-5 (no further info).
Ijspeert, A.J., "Central pattern generators for locomotion control in animals and robots: a review," *Preprint of Neural Networks*, vol. 21, No. 4, pp. 642-653 (2008).
International Preliminary Report on Patentability for International Application No. PCT/US2010/047279; dated Mar. 15, 2012.
International Search Report and Written Opinion for International Application No. PCT/US2009/055600, dated Apr. 29, 2010.
International Search Report and Written Opinion for International Application No. PCT/US2010/047279; dated Jan. 19, 2011.
International Search Report and Written Opinion for International Application No. PCT/US2011/031105, dated Oct. 11, 2011.
International Search Report for PCT/US2010/022783, "Model-Based Neuromechanical Controller for a Robotic Leg", dated May 4, 2010.
Ivashko, D.G. et al., "Modeling the spinal cord neural circuitry controlling cat hindlimb movement during locomotion," *Neurocomputing*, 52-54, pp. 621-629 (2003).
Johansson, J.L. et al., "A Clinical Comparison of Variable-Damping and Mechanically Passive Prosthetic Knee Devices," Variable-Damping vs. Mechanically Passive Prosthetic Knees, *Am J Phys Med Rehabil* 84(8):1-13, (Aug. 2005).
Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).
Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).
Kadaba, M.P. et al., "Measurement of Lower Extremity Kinematics During Level Walking," *Journal of Orthapedic Research*, pp. 383-392, 1990.
Kadaba, M.P. et al., "Repeatability of Kinematic, Kinetic, and Electromyographic Data in Normal Adult Gait," *Journal of Orthapedic Research*, pp. 849-860, 1989.
Kajita, S. et al., "A Hop towards Running Humanoid Biped," Proceedings of the 2004 IEEE International Conference on Robotics & Automation, pp. 629-635, 2004.
Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.
Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).
Kaneko, K. et al., "Humanoid Robot HRP-2," Proceedings of the 2004 IEEE International Conference on Robotics & Automation, pp. 1083-1090 (Apr. 2004).
Kapti, A.O. et al., "Design and control of an active artificial knee joint," *Mechanism and Machine Theory*, vol. 41, pp. 1477-1485 (2006).
Katic, D. et al., "Survey of Intelligent Control Techniques for Humanoid Robots," *Journal of Intelligent and Robotic Systems*, vol. 37, pp. 117-141 (2003).
Kerrigan, D.C. et al., "A refined view of the determinants of gait: Significance of heel," *Archives of Physical Medicine and Rehabilitation*, vol. 81, Issue 8, pp. 1077-1080 (Aug. 2000).
Kerrigan, D.C. et al., "Quantification of pelvic rotation as a determinant of gait," Archives of Physical Medicine and Rehabilitation, vol. 82, Issue 2, pp. 217-220 (Feb. 2001).
Khatib, O. et al., "Coordination and Decentralized Cooperation of Multiple Mobile Manipulators," *Journal of Robotic Systems*, 13(11): 755-764 (1996).
Khatib, O. et al., "Whole-Body Dynamic Behavior and Control of Human-Like Robots," *International Journal of Humanoid Robotics*, vol. 1, No. 1, pp. 29-43 (2004).
Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).
Kim, J.-H. et al., "Realization of Dynamic Walking for the Humaniod Robot Platform KHR-1," *Advanced Robotics*, 18(7): 749-768, (2004).
Kirkwood, C.A. et al., "Automatic detection of gait events: a case study using inductive learning techniques,"*J. Biomed. Eng.*, vol. 11, pp. 511-516 (Nov. 1989).

(56) References Cited

OTHER PUBLICATIONS

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.
Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.
Klute, G.K. et al., "Artificial Muscles: Actuators for Biorobotic Systems," *The International Journal of Robotics Research*, 21(4): 295-309 (2002).
Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).
Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.
Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).
Klute, G.K. et al., "Variable Stiffness Prosthesis for Transtibial Amputees," Dept of Veteran Affairs, Seattle, WA USA, 2 pages (2003).
Klute, G.K. et al., "Artificial Muscles: Actuators for Lower Limb Prostheses," Abstract in: Proceedings of the $2^{nd}$ Annual Meeting of the VA Rehabilitation Research and Development Service, Washington, D.C., Feb. 20-22, 2000, p. 107.
Klute, G.K. et al., "Mechanical properties of prosthetic limbs: Adapting to the patient," *Journal of Rehabilitation Research and Development*, vol. 38, No. 3, pp. 299-307 (May/Jun. 2001).
Koganezawa, K. et al., Biomedical Engineering 1987, 2.3: Control Aspects of Artificial Leg, pp. 71-85 (1987).
Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.
Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).
Kuo, A.D., "A Simple Model of Bipedal Walking Predicts the Preferred Speed—Step Length Relationship," *Transactions of the ASME*, vol. 123, pp. 264-269 (Jun. 2001).
Kuo, A.D., "Energetics of Actively Powered Locomotion Using the Simplest Walking Model," *Journal of Biomechanical Engineering*, vol. 124, pp. 113-120 (Feb. 2002).
Lafortune, M.A., "Three-Dimensional Acceleration of the Tibia During Walking and Running," *J. Biomechanics*, vol. 24, No. 10, pp. 877-886 (1991).
LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.
Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Light, L.H. et al., "Skeletal Transients on Heel Strike in Normal Walking with Different Footwear," *J. Biomechanics*, vol. 13, pp. 477-480 (1980).
Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.
Lloyd, R. et al., "Kinetic changes associated with load carriage using two rucksack designs," *Ergonomics*, vol. 43, No. 9, pp. 1331-1341 (2000).
Luinge, H.J., *Inertial Sensing of Human Movement*, Twente University Press, Enschede, the Netherlands, 80 pages (Feb. 15, 1973).
Lundberg, A., "Reflex control of stepping," The Norwegian Academy of Science and Letters, The Nansen Memorial Lecture, Oct. 10, 1968, 40 pages.
Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.
Maganaris, C.N., "Force-length characteristics of in vivo human skeletal muscle," *Acta Physiol Scand*, 172: 279-285 (2001).
Maganaris, C.N., "Force-Length Characteristics of the In Vivo Human Gastroenemius Muscle," *Clinical Anatomy*, 16: 215-223 (2003).
Martens, W.L.J., "Exploring the Information Content and Some Applications of Body Mounted Piezo-Resistive Accelerometers," PhyVision b.v., Gernert, The Netherlands, pp. 9-12, no date given.
Maufroy, C. et al., "Towards a general neural controller for quadrupedal locomotion," *Neural Networks*, 21: 667-681 (2008).
Mayagoitia, R.E. et al., "Accelerometer and rate gyroscope measurement of kinematics: an inexpensive alternative to optical motion analysis systems," *Journal of Biomechanics*, 35: 537-542 (2002).
McFadyen, B.J. et al., "An Integrated Biomechanical Analysis of Normal Stair Ascent and Descent," *J. Biomechanics*, vol. 21, No. 9, pp. 733-744 (1988).
McGeer, T., "Passive Dynamic Walking," The International Journal of Robotics Research, 9, pp. 62-88 (1990).
McGeer, T., Chapter 4: "Principles of Walking and Running," *Advances in Comparative and Environmental Physiology*, Chapter 4, pp. 113-139 (1992).
McIntosh, A.S. et al., "Gait dynamics on an inclined walkway," *J. Biomechanics*, vol. 39, Issue 13, pp. 2491-2502 (2006).
McMahon, T.A. et al., "Groucho Running," *J. Appl. Physiol.* 62(6) pp. 2326-2337 (1987).
McMahon, T.A. et al., "The Mechanics of Running: How Does Stiffness Couple with Speed?" *J. Biomechanics*, vol. 23, Suppl. 1, pp. 65-78 (1990).
Minassian, K. et al., "Human lumbar cord circuitries can be activated by extrinsic tonic input to generate locomotor-like activity," *Human Movement Science*, 26: 275-295 (2007).
Mochon, S. et al., "Ballistic Walking," *J. Biomechanics*, vol. 13, pp. 49-57 (1980).
Molen, N.H., "Energy/Speed Relation of Below-Knee Amputees Walking on a Motor-Driven Treadmill," *Physiol*, 31: 173-185 (1973).
Morris, J.R.W., "Accelerometry—A Technique for the Measurement of Human Body Movements," *J. Biomechanics*, vol. 6, pp. 729-736 (1973).
Muraoka, T. et al., "Muscle fiber and tendon length changes in the human vastus lateralis during show pedaling," *J. Appl. Physiol.*, 91: 2035-2040 (2001).
Nakagawa, A., "Intelligent Knee Mechanism and the Possibility to Apply the Principle to the Other Joints," paper presented at the Proceedings of the $20^{th}$ Annual International Conference of the IEEE Engineering in Medicine and Biology Society, 20(5): 2282-2287 (1998).
Neal, R. M. et al., "A View of the EM Algorithm That Justifies Incremental, Sparse, and Other Variants," pp. 1-14, no date given.
Ng, S.K. et al., "Fuzzy Model Identification for Classification of Gait Events in Paraplegics," IEEE Transactions on Fuzzy Systems, 5(4) (1997).

(56) References Cited

OTHER PUBLICATIONS

Nielsen, D.H. et al., "Comparison of Energy Cost and Gait Efficiency during Ambulation in Below-Knee Ampuees Using Different Prosthetic Feet," JPO, 1:24-31, http://www.oandp.org/jpo/library/1989_01_024.asd, Retrieved on: Feb. 7, 2012.
Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).
Ogihara, N., and Yamazaki, N., "Generation of Human Bipedal Locomotion by a Bio-Mimetic Neuro-Musculo-Skeletal Model," *Biol. Cybern.*, 84: 1-11 (2001).
Palmer, M.L., "Sagittal Plane Characterization of Normal Human Ankle Function Across a Range of Walking Gait Speeds," Unpublished master's thesis, Massachusetts Institute of Technology, Massachusetts, 71 pages (2002).
Paluska, D., and Herr H., "The Effect of Series Elasticity on Actuator Power and Work Output: Implications for Robotic and Prosthetic Joint Design," Robotics and Autonomous Systems, 54:667-673 (2006).
Paluska, D., and Herr, H., "Series Elasticity and Actuator Power Output," paper presented at the Proceedings of the 2006 IEEE International Conference on Robotics and Automation, 4 pages (May 2006).
Pang, M.Y.C. and Yang, J.F., "The Initiation of the Swing Phase in Human Infact Stepping: Importance of Hip Position and Leg Loading," *Journal of Physiology*, 528(2):389-404 (2000).
Pasch, K.A., et al., "On the drive systems for high performance machines," *AMSE J. Mechanisms, Transmissions, and Automation in Design* 106(1):102-108 (Mar. 1984).
Paul, C., et al., "Development of a Human Neuro-Musculo-Skeletal Model for Investigation of Spinal Cord Injury," *Biol. Cybern.*, 93:153-170 (2005).
Pearson, K., et al., "Assessing Sensory Function in Locomotor Systems Using neurp-mechanical Simulations," *Trends in Neurosciences*, 29(11): 626-631 (2006).
Pearson, K.G., "Generating the Walking Gait: Role of Sensory Feedback," *Progress in Brain Research*, 143:123-129 (2004).
Peeraer, L., et al., "Development of EMG-based mode and intent recognition algorithms for a computer-controlled above-knee prosthesis," J. Biomed. Eng., 12: 178-182 (1990).
Perry, J., et al., "Efficiency of Dynamic Elastic Response Prosthetic Feet," *Journal of Rehabilitation Research*, 30(1):137-143 (1993).
Petrofsky, J. S., et al., "Feedback Control System for Walking in Man," *Comput. Biol. Med.* 14(2):135-149 (1984).
Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).
Popovic, D. and Sinkjaer, T., "Control of Movement for the Physically Disabled: Control for Rehabilitation Technology," (Springer Publisher) pp. 270-302, No date given.
Popovic, D., et al., "Control Aspects of Active Above-Knee Prosthesis," *Int. J. Man-Machine Studies*, 35:751-767 (1991).
Popovic, M., et al., "Angular Momentum Primitives for Human Walking: Biomechanics and Control," paper presented at the Proceedings IEEE/RSJ International Conference on Intelligent Robots and Systems, Sendai, Japan, pp. 1685-1691 (2004).
Popovic, M., et al., "Angular Momentum Regulation During Human Walking: Biomechanics and Control," paper presented at the Proceedings IEEE International Conference on Robotics and Automation, New Orleans, LA, pp. 2405-2411 (2004).
Popovic, M., et al., "Conservation of Angular Momentum During Human Locomotion," *MIT Artificial Intelligence Laboratory*, pp. 231-232 (2002).
Popovic, M.B. and Herr, H., "Global Motion Control and Support Base Planning," MIT pp. 1-8, no date given.
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," MIT, pp. 1-16, no date given.
Popovic, M.R., et al., "Gait Identification and Recognition Sensor," paper presented at the Proceedings of $6^{th}$ Vienna International Workshop on Functional Electrostiumlation (Sep. 1998).
Pratt, G.A. and Williamson, M.M., "Series Elastic Actuators." Paper presented at the meeting of the IEEE, pp. 399-406 (1995).
Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Prochazka, A. and Yakovenko, S., "The Neuromechanical Tuning Hypothesis," *Progress in Brain Research*, 165: 257-267 (2007).
Prochazka, A., et al., "Positive Force Feedback Control of Muscles," *The American Physiological Society* 77:3226-3236 (1997).
Prochazka, A., et al., "Sensory Control of Locomotion: Reflexes Versus Higher-Level Control," *Sensorimotor Control of Movement and Posture*, pp. 357-367 (2002).
Raibert, M.H., "Legged Robots that Balance," MIT Press, Cambridge, MA, p. 89 (1985).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).
Robinson, D.W., "Design and Analysis of Series Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man, and Cybernetics—Part A: Systems and Humans*, 31(3):210-222 (2001).
Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2):617-639 (2006).
Rybak, I.A., et al., "Modelling Spinal Circuitry Involved in Locomotor Pattern Generation: Insights from the Effects of Afferent Stimulation," *J. Physiol.*, 577(2):641-658 (2006).
Sanderson, D.J. and Martin. P.E., "Lower Extremity Kinematic and Kinetic Adaptations in Unilateral Below-Knee Amputees During Walking," *Gait & Posture*, 6(2):126-136 (1997).
Sanger, T.D., "Human Arm Movements Described by a Low-Dimensional Superposition of Principal Components," *The J. of Neuroscience*, 20(3):1066-1072 (2000).
Saranli, U., et al., "RHex: A Simple and Highly Mobile Hexapod Robot," *The International Journal of Robotics Research*, pp. 616-631 (2001).
Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).

(56) References Cited

OTHER PUBLICATIONS

Saxena, S. C., and Mukhopadhyay, P., "E.M.G. operated electronic artificial-leg controller," Med. & Biol. Eng. & Comput., 15: 553-557 (1977).
Schaal, S. and Atkeson, C.G., "Constructive Incremental Learning from Only Local Information," Neural Computation, 10(8): 2047-2084 (1998).
Schaal, S., "Is Imitation Learning the Route to Humanoid Robots?", Trends in Cognitive Sciences, 3: 233-242 (1999).
Scott, S.H. and Winter, D.A., "Biomechanical Model of the Human Foot: Kinematics and Kinetics During the Stance Phase of Walking," J. Biomechanics, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16 (no date given).
Seyfarth, A., et al., "A Movement Criterion for Running," J. of Biomechanics, 35: 649-655 (2002).
Seyfarth, A., et al., "Stable Operation of an Elastic Three-Segment Leg," Biol. Cybern., 84: 365-382 (2001).
Seyfarth, A., et al., "Swing-Leg Retraction: A Simple Control Model for Stable Running," The J. of Experimental Biology, 206: 2547-2555 (2003).
Sinkjaer, T., et al., "Major role for sensory feedback in soleus EMG activity in the stance phase of walking in man," Journal of Physiology, 523.3: 817-827 (2000).
Skinner, H.B., and Effeney, D.J., "Gait Analysis in Amputees," American Journal of Physical Medicine, 64(2): 82-89 (1985).
Smidt, G.L., et al., "An Automated Accelerometry System for Gait Analysis," J. Biomechanics, 10: 367-375 (1977).
Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5 (no year given).
Stepien, J., et al., "Activity Levels Among Lower-Limb Amputees: Self-Report Versus Step Activity Monitor," Arch. Phys. Med. Rehabil., 88: 896-900 (2007).
Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).
Sup, F., et al., "Design and Control of a Powered Transfemoral Prosthesis," The International Journal of Robotics Research, 27(2): 263-273 (2008).
Supplementary European Search Report Application No. 10736533.0, "Powered Artificial Knee with Agonist-Antagonist Actuation," dated Aug. 16, 2013.
Supplementary European Search Report Application No. 10736550.0, "Model-Based Neuromechanical Controller for a Robotic Leg," dated Aug. 1, 2013.
Taga, G., "A model of the neuro-musculo-skeletal system for human locomotion," Biol. Cybern., 73: 97-111 (1995).
Takayuki, F., et al., "Biped Locomotion using Multiple Link Virtual Inverted Pendulum Model," T.IEE Japan, 120-C (2): 208-214 (2000).
Thoroughman, K., and Shadmehr, R., "Learning of action through adaptive combination of motor primitives," Nature, 407: 742-747(2000).
Tomović, R, and McHee, R.B., "A Finite State Approach to the Synthesis of Bioengineering Control Systems," IEEE Transactions on Human Factors in Electronics, 7(2): 65-69 (1966).
Tong, K., and Granat, M., "A practical gait analysis system using gyroscopes," Medical Engineering & Physics, 21: 87-94 (1999).
Türker, K., "Electromyography: Some Methodological Problems and Issues," Phys. Ther., 73: 698-710 (1993).

Van den Bogert, A. J., "Exotendons for Assistance of Human Locomotion," Biomedical Engineering OnLine, BioMed Central, 2(17):1-8 (2003).
Van den Bogert, A. J., et al., "A Method for Inverse Dynamic Analysis Using Accelerometry," J. Biochemechanics, 29(7): 949-954 (1996).
Veltink, P.H., et al., "The Feasibility of Posture and Movement Detection by Accelerometry," paper presented at the IEEE meeting (1993).
Vukobratovic, M., and Juricic, D., "Contribution to the Synthesis of Biped Gait," paper presented at the IEEE Transactions on Bio-Medical Engineering, BME-16(1) (Jan. 1969).
Vukobratovic, M., and Stepanenko, J., Mathematical Models of General Anthropomorphic Systems, Mathematical Biosciences, 17: 191-242 (1973).
Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).
Waters, R.L., et al., "Energy Cost of Walking of Amputees: The Influence of Level of Amputation," The Journal of Bone and Joint Surgery, 58A(1): 42-46 (1976).
Wilkenfeld, A., "Biologically Inspired Autoadaptive Control of a Knee Prosthesis," unpublished doctoral dissertation, Massachusetts Institute of Technology, Cambridge, MA (2000).
Wilkenfeld, A., and Herr, H., "An Auto-Adaptive External Knee Prosthesis," MIT Lab., (No date given).
Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).
Willemsen, A.Th.M., et al., "Real-Time Gait Assessment Utilizing a New Way of Accelerometry," J. Biomechanics, 23(8):859-863 (1990).
Williams, B.C., et al., "Mode Estimation of Model-Based Programs: Monitoring Systems with Complex Behavior," paper submitted to Massachusetts Institute of Technology, Cambridge, MA, (No date given).
Williamson, M.M., "Series Elastic Actuators," A.I. Technical Report # 1524 submitted to Massachusetts Institute of Technology, Cambridge, Massachusetts (Jan. 1995).
Winter, D.A., "Energy Generation and Absorption at the Ankle and Knee during Fast, Natural, and Slow Cadences," Clinical Orthopedics and Related Research, 175: 147-154 (1983).
Winter, D.A., and Robertson, D.G.E., "Joint Torque and Energy Patterns in Normal Gait," Biol. Cybernetics, 29:137-142 (1978).
Winter, D.A., and Sienko, S.E., "Biomechanics of Below-Knee Amputee Gait," J. Biomechanics, 21(5):361-367 (1988).
Wisse, M., "Essentials of Dynamic Walking: Analysis and Design of Two-legged Robots," 195 pgs, (2004).
Woodward, M.I. and Cunningham, J.L., "Skeletal Accelerations Measured During Different Exercises," Proc. Instn. Mech. Engrs., 207: 79-85 (1993).
Wu, G. and Ladin, Z., "The Study of Kinematic Transients in Locomotion Using the Integrated Kinematic Sensor," IEEE Transactions on Rehabilitation Engineering, 4(3):193-200 (1996).
Yakovenko, S., et al., "Contribution of Stretch Reflexes to Locomotor Control: A Modeling Study," Biol. Cybern., 90: 146-155 (2004).
Yun, X., "Dynamic State Feedback Control of Constrained Robot Manipulators." Paper presented at the Proceedings of the $27^{th}$ Conference on Decision and Control, Austin, TX (Dec. 1988).
Zlatnik, D., et al., "Finite-State Control of a Trans-Femoral (TF) Prosthesis," IEEE Transactions on Control Systems Technology, 10(3): 408-420 (2002).
Non-Final Office Action from U.S. Appl. No. 15/091,895, "Artificial Ankle-Foot System With Spring, Variable-Damping, and Series-Elastic Actuator Components," dated Jan. 16, 2018.

\* cited by examiner

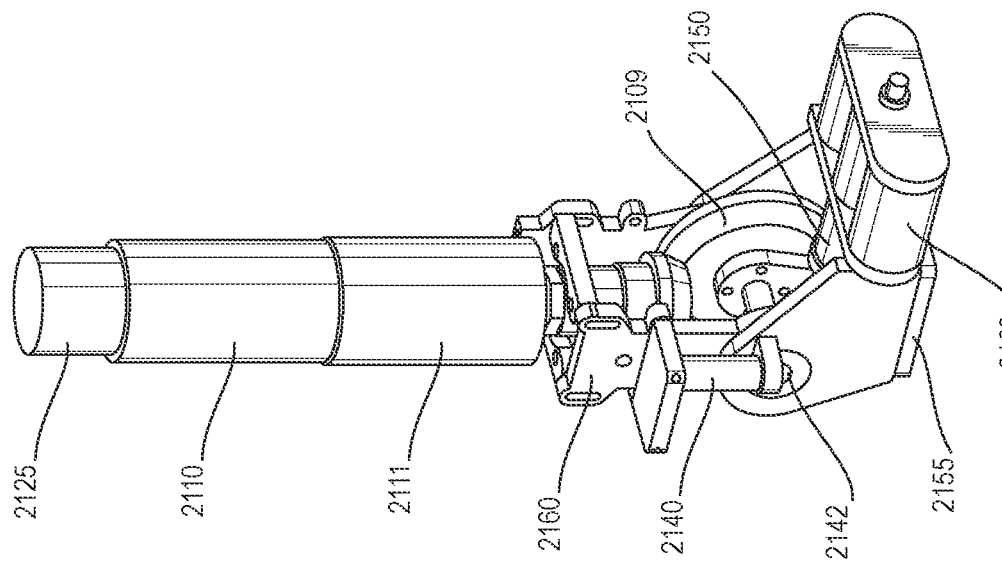
FIG. 21
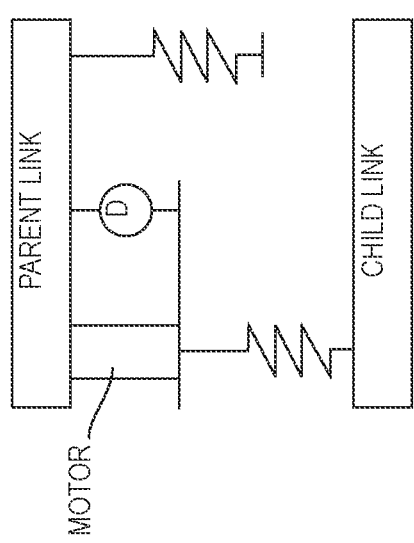
FIG. 19
FIG. 20

ARTIFICIAL HUMAN LIMBS AND JOINTS EMPLOYING ACTUATORS, SPRINGS AND VARIABLE-DAMPER ELEMENTS

RELATED APPLICATIONS

This application is a divisional of U.S. application Ser. No. 13/171,307, filed Jun. 28, 2011, which is a continuation of U.S. application Ser. No. 11/395,448, filed Mar. 31, 2006, now abandoned, which claims the benefit of U.S. Application No. 60/666,876, filed Mar. 31, 2005, and 60/704,517, filed Aug. 1, 2005. The entire teachings of the above applications are incorporated herein by reference.

FIELD OF THE INVENTION

This invention relates generally to prosthetic devices and artificial limb systems, including robotic, orthotic, exoskeletal limbs, and more particularly, although in its broader aspects not exclusively, to artificial ankle, knee, and hip joints.

BACKGROUND

In the course of the following description, reference will be made to the papers, patents and publications presented in a list of references at the conclusion of this specification. When cited, each listed reference will be identified by a numeral within curly-braces indicating its position within this list.

As noted in {1} {2} {3} {4}, an artificial limb system that mimics a biological limb ideally needs to fulfill a diverse set of requirements. The artificial system must be a reasonable weight and have a natural morphological shape, but still have an operational time between refueling or battery recharges of at least one full day. The system must also be capable of varying its position, impedance, and motive power in a comparable manner to that of a normal, healthy biological limb. Still further, the system must be adaptive, changing its characteristics given such environmental disturbances as walking speed and terrain variation. The embodiments of the invention which are described in this specification employ novel actuator and limb architectures capable of achieving these many requirements.

From recent biomechanical studies {1} {2} {3}, researchers have determined that biological joints have a number of features. Among these are:
  (a) The ability to vary stiffness and damping.
  (b) The ability to generate large amounts of both positive and negative mechanical work.
  (c) The ability to produce large amounts of nonconservative power and torque when needed.

An example of the use of more than one control strategy in a single biological joint is the ankle {1} {2}. For level ground ambulation, the ankle behaves as a variable stiffness device during the early to midstance period, storing and releasing impact energies. Throughout terminal stance, the ankle acts as a torque source to power the body forward. In distinction, the ankle varies damping rather than stiffness during the early stance period of stair descent. These biomechanical findings suggest that in order to mimic the actual behavior of a human joint or joints, stiffness, damping, and nonconservative, motive power must be actively controlled in the context of an efficient, high cycle-life, quiet and cosmetic biomimetic limb system, be it for a prosthetic or orthotic device. This is also the case for a biomimetic robotic limb since it will need to satisfy the same mechanical and physical laws as its biological counterpart, and will benefit from the same techniques for power and weight savings.

In the discussion immediately below, the biomechanical properties of three human joints, the ankle, knee and hip, will be described in some detail to explain the insights that have guided the design and development of the specific embodiments of the invention and to define selected terms that will be used in this specification.

Joint Biomechanics: The Human Ankle

Understanding normal walking biomechanics provides the basis for the design and development of the artificial ankle joint and ankle-foot structures that embody the invention. Specifically, the function of human ankle under sagittal plane rotation is described below for different locomotor conditions including level-ground walking and stair/slope ascent and descent. From these biomechanical descriptions, the justifications for key mechanical components and configurations of the artificial ankle structures and functions embodying the invention may be better understood.

Level-Ground Walking

A level-ground walking gait cycle is typically defined as beginning with the heel strike of one foot and ending at the next heel strike of the same foot {8}. The main subdivisions of the gait cycle are the stance phase (about 60% of the cycle) and the subsequent swing phase (about 40% of the cycle) as shown in FIG. 1. The swing phase represents the portion of the gait cycle when the foot is off the ground. The stance phase begins at heel-strike when the heel touches the floor and ends at toe-off when the same foot rises from the ground surface. Additionally, we can further divide the stance phase into three sub-phases: Controlled Plantar flexion (CP), Controlled Dorsiflexion (CD), and Powered Plantar flexion (PP).

Each phase and the corresponding ankle functions which occur when walking on level ground are illustrated in FIG. 1. The subdivisions of the stance phase of walking, in order from first to last, are: the Controlled Plantar flexion (CP) phase, the Controlled Dorsiflexion (CD) phase, and the Powered Plantar flexion (PP) phase.

CP begins at heel-strike illustrated at 103 and ends at foot-flat at 105. Simply speaking, CP describes the process by which the heel and forefoot initially make contact with the ground. In {1} {3}, researchers showed that CP ankle joint behavior was consistent with a linear spring response where joint torque is proportional to joint position. The spring behavior is, however, variable; joint stiffness is continuously modulated by the body from step to step.

After the CP period, the CD phase continues until the ankle reaches a state of maximum dorsiflexion and begins powered plantarflexion PP as illustrated at 107 Ankle torque versus position during the CD period can often be described as a nonlinear spring where stiffness increases with increasing ankle position. The main function of the ankle during CD is to store the elastic energy necessary to propel the body upwards and forwards during the PP phase {9} {3}.

The PP phase begins after CD and ends at the instant of toe-off illustrated at 109. During PP, the ankle can be modeled as a catapult in series or in parallel with the CD spring or springs. Here the catapult component includes a motor that does work on a series spring during the latter half of the CD phase and/or during the first half of the PP phase. The catapult energy is then released along with the spring energy stored during the CD phase to achieve the high plantar flexion power during late stance. This catapult behavior is necessary because the work generated during PP is more than the negative work absorbed during the CP and CD phases for moderate to fast walking speeds {1} {2} {3} {9}.

During the swing phase, the final 40% of the gait cycle, which extends from toe-off at 109 until the next heel strike at 113, the foot is lifted off the ground.

Stair Ascent and Descent

Because the kinematic and kinetic patterns at the ankle during stair ascent/descent are significantly different from that of level-ground walking {2}, a separate description of the ankle-foot biomechanics is presented in FIGS. 2 and 3.

FIG. 2 shows the human ankle biomechanics during stair ascent. The first phase of stair ascent is called Controlled Dorsiflexion 1 (CD 1), which begins with foot strike in a dorsiflexed position seen at 201 and continues to dorsiflex until the heel contacts the step surface at 203. In this phase, the ankle can be modeled as a linear spring.

The second phase is Powered Plantar flexion 1 (PP 1), which begins at the instant of foot flat (when the ankle reaches its maximum dorsiflexion at 203) and ends when dorsiflexion begins once again at 205. The human ankle behaves as a torque actuator to provide extra energy to support the body weight.

The third phase is Controlled Dorsiflexion 2 (CD 2), in which the ankle dorsiflexes until heel-off at 207. For the CD 2 phase, the ankle can be modeled as a linear spring.

The fourth and final phase is Powered Plantar flexion 2 (PP 2) which begins at heel-off 207 and continues as the foot pushes off the step, acting as a torque actuator in parallel with the CD 2 spring to propel the body upwards and forwards, and ends when the toe leaves the surface at 209 to being the swing phase that ends at 213.

FIG. 3 shows the human ankle-foot biomechanics for stair descent. The stance phase of stair descent is divided into three sub-phases: Controlled Dorsiflexion 1 (CD1), Controlled Dorsiflexion 2 (CD2), and Powered Plantar flexion (PP).

CD1 begins at foot strike illustrated at 303 and ends at foot-flat 305. In this phase, the human ankle can be modeled as a variable damper. In CD2, the ankle continues to dorsiflex forward until it reaches a maximum dorsiflexion posture seen at 307. Here the ankle acts as a linear spring, storing energy throughout CD2. During PP, which begins at 307, the ankle plantar flexes until the foot lifts from the step at 309. In this final PP phase, the ankle releases stored CD2 energy, propelling the body upwards and forwards. After toe-off at 309, the foot is positioned controlled through the swing phase until the next foot strike at 313.

For stair ascent depicted in FIG. 2, the human ankle-foot can be effectively modeled using a combination of an actuator and a variable stiffness mechanism. However, for stair descent, depicted in FIG. 3, a variable damper needs also to be included for modeling the ankle-foot complex; the power absorbed by the human ankle is much greater during stair descent than the power released by 2.3 to 11.2 J/kg {2}. Hence, it is reasonable to model the ankle as a combination of a variable-damper and spring for stair descent {2}.

Joint Biomechanics: The Human Knee

There are five distinct phases to knee operation throughout a level-ground walking cycle {8}. To further motivate the hybrid actuator design described herein, a description of these phases is included.

1. Beginning at the time the heel strikes as indicated at 403 in FIG. 4, the stance knee begins to flex slightly. This flexion period, called the Stance Flexion phase, allows for shock absorption upon impact as well as to keep the body's center of mass at a more constant vertical level throughout the stance period. During this phase, the knee acts as a spring, storing energy in preparation for the Stance Extension phase.

2. After maximum flexion is reached in the stance knee as indicated at 404, the joint begins to extend, until maximum extension is reached at 406. This knee extension period is called the Stance Extension phase. Throughout approximately the first 60% of Stance Extension, the knee acts as a spring, releasing the stored energy from the Stance Flexion phase of gait. This first release of energy corresponds to power output indicated at 501 in FIG. 5. During approximately the last 30% of Stance Extension, the knee absorbs energy in a second spring and then that energy is released during the next gait phase, or Pre-Swing, that begins at 406.

3. During late stance or Pre-Swing, the knee of the supporting leg begins its rapid flexion period in preparation for the swing phase. During early Pre-Swing, as the knee begins to flex in preparation for toe-off, the stored elastic energy from Stance Extension is released. This second release of energy corresponds to power output level indicated at 503 in FIG. 5.

4. As the hip is flexed, and the knee has reached a certain angle in Pre-Swing, the leg leaves the ground and the knee continues to flex as indicated at 407 in FIG. 4. At the time of toe-off at 407, the Swing Flexion phase of gait begins. Throughout this period, knee power is generally negative where the knee's torque impedes knee rotational velocity. During early Swing Flexion, the knee behaves as a variable damper, and during terminal Swing Flexion, the knee can be modeled as a spring, storing energy in preparation for early Swing Extension.

5. After reaching a maximum flexion angle during swing, the knee begins to extend forward as indicated at 408. During the early Swing Extension period, the spring energy stored during late Swing Flexion is then released, resulting in power output level indicated at 505 in FIG. 5. During the remainder of Swing Extension, the human knee outputs negative power (absorbing energy) to decelerate the swinging leg in preparation for the next stance period. After the knee has reached full extension, the foot once again is placed on the ground, and the next walking cycle begins at 410.

Joint Biomechanics: The Human Hip

FIGS. 6 and 7 graphically depict human hip biomechanics for level ground walking Hip position (radians) is plotted in FIG. 6 and hip power (watts) is shown in FIG. 7, and show the spring-like behavior of the hip in walking Maximum hip power absorption occurs as indicated at 702 during terminal hip extension, and maximum hip power output occurs during active hip flexion near toe-off as indicated at 704 to drive the lower leg from the walking surface.

As discussed in more detail later, the hip can be modeled with a spring in parallel with a motor system. The parallel spring generally stores energy during hip extension and then releases that energy to power hip flexion. To the extent to which the desired joint behavior deviates from a conservative spring response, the hip model includes a parallel motor system designed to modulate stiffness, damping and power about the natural spring output.

Prior Art Leg Systems

The current state of the art in prosthetic leg systems include a knee joint that can vary its damping via magnetorheological fluid {5}, and a carbon fiber ankle which has no active control, but that can store energy in a spring structure for return at a later point in the gait cycle (e.g. the Flex-Foot or the Seattle-Lite) {4} {6}. None of these systems are able to add energy during the stride to help keep the body moving forward or to reduce impact losses at heel strike. In the case of legged robotic systems, the use of the Series Elastic Actuator (SEA) enables robotic joints to control their position and torque, such that energy may be added to the system as needed {7}. In addition, the SEA can emulate a physical spring or damper by applying torques based on the position or velocity of the joint. However, for most applications, the SEA requires a tremendous amount of electric power for its operation, resulting in a limited operational life or an overly large power supply. Robotic joint designs in general use purely active components and often do not conserve electrical power through the use of passive-elastic and variable-impedance devices.

SUMMARY OF THE INVENTION

In the construction of a biologically realistic limb system that is high performance, light weight, quiet and energetically efficient, embodiments of the invention to be described below employ passive-elastic, variable-damping, and motor elements. Since it is desirable to minimize the overall weight of the limb design, the efficiency of the system is critical, especially given the poor energy density of current power supplies, e.g. lithium-ion battery technology. By understanding human biomechanics, the lightest, most energy efficient hybrid actuator design can be achieved.

The illustrative embodiments to be described employ Biomimetic Hybrid Actuators in biologically-inspired musculoskeletal architectures and use an electric motor for supplying positive energy to and storing negative energy from one or more joints which connect skeletal members, as well as elastic elements such as springs, and controllable variable damper components, for passively storing and releasing energy and providing adaptive stiffness to accommodate level ground walking as well as movement on stairs and surfaces having different slopes.

These hybrid actuators manipulate first and second skeletal members connected at one or more joints for movement relative to one another. A motor applies a force to move one member with respect to the other. One or more passive elastic members are connected between the skeletal members for storing energy when the members move relative to one another in one direction and for releasing energy when the members relative to one another in the opposite direction, and one or more controllable variable damping elements dissipate mechanical energy to arrest the relative motion of the first and second members at controllable times.

Some of the embodiments provide additional force using a catapult mechanism in which the motion of the members is arrested by a controllable damping element while the motor stores energy in one or more elastic members and the damping element thereafter releases the members which are then moved by the energy stored in the elastic member.

One or more damping elements may be operatively connected in parallel with the motor to arrest its motion while energy is stored in one or more elastic members and thereafter the motor parallel damping element releases the motor to release the energy previously stored in the elastic member.

The hybrid actuator may employ an elastic member operatively connected in series with a controllable damping member. When the controllable damping member exhibits a higher damping level, energy is stored in the series elastic member and thereafter, when the controllable damping member exhibits a lower damping level, energy is released from the series elastic member.

The motor in the hybrid actuator may apply torque to a joint or joints through a gearbox and a first controllable variable damping element can be employed to arrest the motion of the motor at controllable times, and a further controllable variable damping element operatively connected between the motor and the gearbox can disconnect the motor and the gearbox at controllable times, such that the gearbox can be used as a damping element to arrest the motion of skeletal members at some times, and be used to apply force to move the members at other times.

The hybrid actuator may be used to implement an artificial ankle joint which connects a foot member for rotation with respect to a shin member, and which includes a motor for applying torque to the ankle joint to rotate the foot member with respect to the shin member, one or more passive elastic members connected between the shin and foot members for storing energy when the foot member rotates about the ankle joint toward the shin member and for releasing energy to apply additional torque to rotate the foot member away from the shin member, and one or more controllable variable damping elements for dissipating mechanical energy to arrest the relative motion of the foot and shin members at controllable times.

An artificial ankle may employ an elastic member operatively connected in series with the motor between the shin member and the foot member to store energy when the relative motion of the foot and shin members is being arrested by a controllable variable damping element and to thereafter apply an additional torque to the ankle joint when the variable damping element no longer arrests the relative motion of the two members.

An artificial ankle may include an elastic member operatively connected in series with the motor between the shin and foot members to store energy when the foot member is moved toward the shin member and to release energy and apply an additional torque to the ankle joint that assists the motor to move the foot member away from the shin member. A controllable damping member may be employed to arrest the motion of the motor to control the amount of energy absorbed by the motor when the foot member is moved toward the shin member.

A hybrid actuator may also be used to implement an artificial knee in which a thigh and shin skeletal member are connected by a knee joint and a motor is used to apply torque to the knee joint to rotate the shin member with respect to the thigh member at controllable times and to absorb energy from the rotation of the shin member with respect to the thigh member at other times. One or more passive elastic members connected between the shin and thigh members may be used to store energy when the shin member rotates toward the thigh member and to thereafter release energy to apply additional torque to the knee joint to rotate the shin member away from the thigh member, and a controllable variable damping element may be used to dissipate mechanical energy to arrest the relative motion of the thigh and shin members at controllable times.

An artificial knee may employ the motor to apply torque to the knee joint to rotate the shin member with respect to the thigh member at controllable times and to absorb energy from the rotation of the shin and thigh members at other times, and further employ an elastic member operatively connected in series with the motor to store energy when the shin and thigh members are forced toward one another, and to release energy and apply an additional torque to aid the motor when the shin member moves away from the thigh member. In addition, a controllable variable damping element may be employed to arrest the motion of the motor to control the amount of energy absorbed by the motor when the foot member is moved toward the shin member.

As artificial knee may further comprise a second elastic member operatively connected between the thigh member and the shin member in series with a second controllable variable damping element that supplies a high level of damping at controllable times to store energy in the second elastic member and a lower level of damping at other times to release the energy stored in the second elastic member.

A further embodiment of the invention may take the form of an artificial hip that consists of a pelvis member, a thigh member and a hip joint that connects the thigh member for rotation with respect to the pelvis member, a motor for applying torque to the hip joint to rotate the thigh member with respect to the pelvis member, and an elastic member operatively connected in series with a controllable variable damping element between the pelvis member and the thigh member, with the controllable variable damping member providing a high level of damping at controllable times to store energy in the elastic member and a lower level of damping at other times to release the energy stored in the second elastic member.

An artificial hip may include a controllable variable damping element for dissipating mechanical energy to arrest the relative motion of the thigh member with respect to the pelvis member at controllable times, and an elastic member operatively connected in series with the motor between the pelvis member and the thigh member to store energy from the motor when the relative motion of the thigh member and the pelvis member is being arrested by the controllable variable damping element and to thereafter apply an additional torque to the joint member when the relative motion of the thigh member with respect to the pelvis member is no longer arrested by the controllable variable damping element.

An artificial hip may employ a motor connected for applying torque to the hip joint to rotate the thigh member with respect to the pelvis member at controllable times and to absorb energy from the rotation of the thigh member with respect to the pelvis member at other times, an elastic member operatively connected in series with the motor between the pelvis member and the thigh member to store energy when the thigh member is rotated upwardly member and to release energy and apply a torque to aid the motor when the thigh member rotates downwardly, and a controllable variable damping element for arresting the motion of the motor to control the amount of energy absorbed by the motor when the foot member is moved toward the shin member.

A Biomimetic Hybrid Actuator may span more than one joint to implement an artificial limb consisting of first, second and third elongated skeletal members, a first joint for connecting the first member for rotation with respect to the second member, a second joint for connecting the second member for rotation with respect to the third member, and a motor connected between the first and third member for applying a force to rotate the first member with respect to the second member about the first joint and to rotate the second member with respect to the third member about the second joint. One or more passive elastic members connected between the first and third members may be employed to store energy when the first and third members move toward one another and to release energy when the members move away from one another, and one or more controllable variable damping elements may be used for dissipating mechanical energy to arrest the motion of the motor or the relative motion of the first and third members at controllable times.

In the detailed description to follow, several Biomimetic Hybrid Actuator variations are described which comprise motor, spring and variable damper components. These actuator embodiments combine active and passive elements in order to achieve high performance with minimal mass. In addition, the use of Hybrid Biomimetic Actuators as mono and poly-articular linear elements is described. In the development of low mass, efficient and quiet biomimetic artificial limbs, biologically-inspired musculoskeletal architectures and hybrid biomimetic actuation strategies comprising motor, spring and variable damper components are important design considerations.

Advantages and Improvements Over Existing Methods:
1. The Flex-Foot, made by Ossur of Reykjavik, Iceland, is a passive carbon-fiber energy storage device that replicates the ankle joint for amputees {7}. The Flex-Foot has an equilibrium position of 90 degrees and a single nominal stiffness value. Embodiments of the present invention which implement artificial ankle joints augment the Flex-Foot by allowing the equilibrium position to be set to an arbitrary angle by a motor and locking this configuration with a clutch or variable damper. The mechanism can also change the stiffness and damping of the prosthesis dynamically.
2. Embodiments of the present invention can provide adaptive stiffness control with respect to the walking speed.
3. Embodiments of the present invention provide adaptive damping control for stair descent and/or downhill walking.
4. Embodiments of the invention have the ability to provide substantial amount of plantar-flexion moment for forward progression during walking using a catapult mechanism.
5. Embodiments of the invention accommodate movement on stairs and surfaces having different slopes.

These and other features and advantages of the present invention will be better understood by considering the following detailed description of twelve illustrative embodiments of the invention. In course of this description, frequent reference will be made to the attached drawings which are briefly described below.

BRIEF DESCRIPTION OF THE DRAWINGS

FIG. 19 is a lumped parameter model a third embodiment of the invention, a biomimetic ankle;

FIG. 20 is a schematic drawing of the third embodiment of the invention;

FIG. 21 is a perspective drawing illustrating the physical implementation of the third embodiment of the invention;

DETAILED DESCRIPTION OF THE INVENTION

Eleven different embodiments of the invention are described which employ an arrangement here called a "Biomimetic Hybrid Actuator" (BHA) that is capable of providing biologically realistic dynamic behaviors. The key mechanical components of the actuator and their general functions are summarized below in Table 1.

TABLE 1

Mechanical components of the Biomimetic Hybrid Actuator System

| Component | Function |
| --- | --- |
| Spring | Store and release energy, absorb shock |
| Motor | Control positive and negative work and power |
| Efficient Variable-Damper or Clutch | Dissipate mechanical energy, control damping, and clutch joint |

Figure 8:
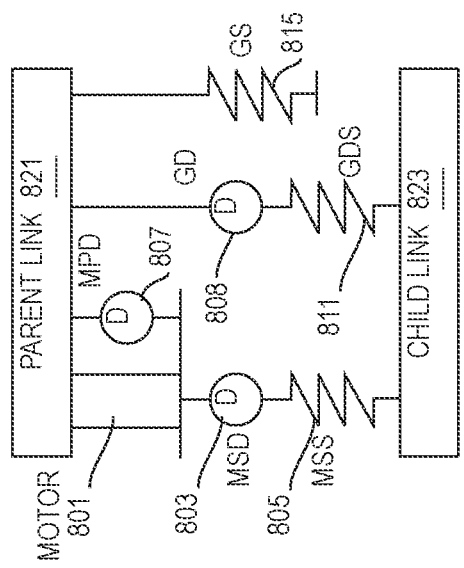
FIG. 8 is a generalized lump parameter model of the components used to implement a hybrid actuator system employed to implement artificial ankles, knees and hips embodying the invention.

As will be described, different combinations and configurations of these elements can provide a variety of biomimetic behaviors. FIG. 8 shows a generalized lumped parameter model which summarizes the elements that make up the various embodiments, and the same symbols are used to in the lumped parameter model diagrams presented for each of the first ten embodiments. In FIG. 8, and in other drawings, the rectangular block labeled "motor" seen at 801 represents a power input such as an electric motor. A circle with the D represents a variable damper or clutch mechanism. In FIG. 8, MSD at 803 is the motor series damper, MPD at 807 is the motor parallel damper, and GD at 808 is the global damper. A jagged line represents a physical spring. MSS at 805 is the motor series spring, GDS at 811 is the global damper spring, and GS at 815 is the global spring. In the description that follows, the same terminology will be used to refer to like components.

The parent and child links at 821 and 823 respectively represent the two segments being acted upon by the hybrid actuator and coupled at a rotary joint. For example, in the case of the ankle joint, the parent link is the shin and the child link is the foot. For knee and ankle joints, the vertical orientation is reversed so that, in the case of the knee joint, the parent link is the shin and the child link is the thigh, and in the case of the hip joint, the parent link is the thigh and the child link is the pelvis.

By performing substitutions on the key elements of the master hybrid actuator depicted in FIG. 8, the lumped parameter models for the first ten embodiments described later can be derived.

Figure 9:
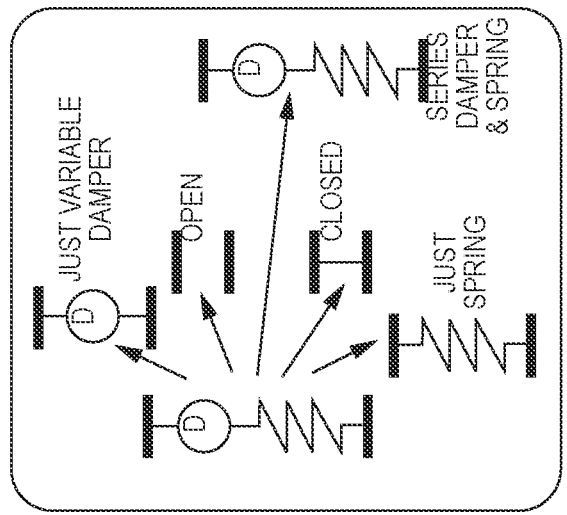
FIG. 9 shows the substitutions that may be made for the series dampers and springs shown in FIG. 8.

FIG. 9 shows the five substitutions that can be made for a damper/clutch and a series spring. The damper/clutch and spring may be replaced by a fixed link, or with nothing at all. The damper/clutch may be used alone or connected in series with a spring. Finally, a spring may be used alone without a damper/clutch.

Figure 10:
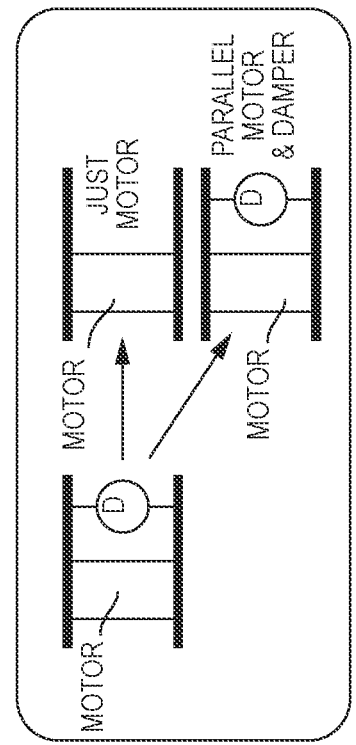
FIG. 10 shows the substitutions that may be made for the motor and parallel damper seen in FIG. 8.

FIG. 10 shows two substitutions that can be made for the parallel motor and damper/clutch; that is, the motor alone may be used, or the motor may be combined with a parallel damper/clutch that brakes or arrests the motor at controlled times during a walking cycle. The motor is preferably and electric motor which can act as a source of power, or can act as a generator absorbing power, at different times during the walking cycle.

Figure 11:
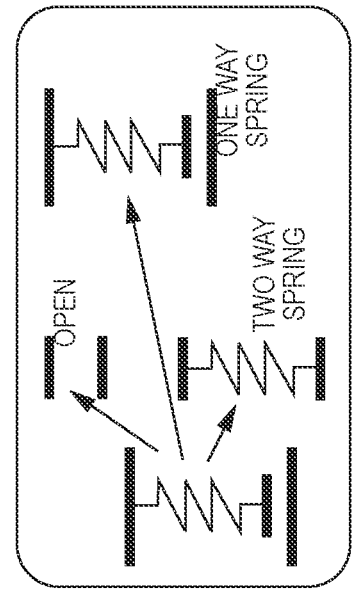
FIG. 11 depicts the substitutions that may be made for the global spring component shown in FIG. 8.

FIG. 11 shows the three substitutions that may be made for a spring element. The spring may be eliminated, or may take the form of a one way spring that is engaged only when the joint moves into a particular position, or may take the form of a two way spring that has different stiffness properties in different joint positions.

It should be understood that additional embodiments of the Biomimetic Hybrid Actuator beyond the variations specifically described below are possible.

Component Implementations

The variable damper or clutch mechanism illustrated in the parameter models by the circled D can be implemented using hydraulic, pneumatic (McKibben actuator), friction, electrorheological, magnetorhelogical, hysteresis brake, or magnetic particle brake damping/clutching strategies. The preferred method for damping control for the Motor Series Damper (MSD) and the Motor Parallel Damper (MPD) is a hysteresis brake because the zero power damping level is negligible. This feature is important because these particular variable damper elements are often behind a mechanical transmission thus low torque, high speed damping or clutching control is desirable. In distinction, the preferred method for damping control for the Global Damper (GD) is a magnetorheological (MR) variable damper since high torque, low speed damping control is desirable. More specifically, the MR fluid, as used in the shear mode, is positioned between a set of rotary plates that shear iron particles suspended in a carrier fluid. As a magnetic field is induced across the fluid layer, the iron particles form chains and increase the shear viscosity, which effectively increases joint dampening. Illustrative examples of such a magnetorheological (MR) variable damper are described in Sandrin et al. U.S. Pat. No. 6,202,806, the disclosure of which is incorporated herein by reference.

The springs represented by jagged lines in the lumped parameter models can be implemented as linear or torsional spring elements. They may be metal die springs, carbon fiber leaf springs, elastomeric compression springs, or pneumatic springs. For this description, the springs are die compression springs.

The motor element could be any electric motor, brushed or brushless. It could also be a hydraulic cylinder, pneumatic cylinder/McKibben system, or other power producing elements such as artificial muscle, piezoelectric or nitinol wire. In the specific embodiments described below, the motor component comprises an electric motor.

It should be understood that the motor and variable damper/clutch functionalities could both be achieved using a single motor system if that system were capable of (1) generating isometric force or torque at low energy consumption and (2) dissipating mechanical energy (damping control) also at low energy consumption. Examples of such a motor system include a pneumatic system (McKibben actuator), hydraulic system or electroactive polymer (EAP) artificial muscle system.

EMBODIMENT DESCRIPTIONS

In the description that follows, examples are provided which illustrate how the invention is employed at the ankle, knee or hip to provide specific ambulatory biomechanics. For each embodiment, a lumped parameter model, a schematic diagram, and a specific physical embodiment are presented.

Embodiment 1

Mechanical Design

Figure 14:
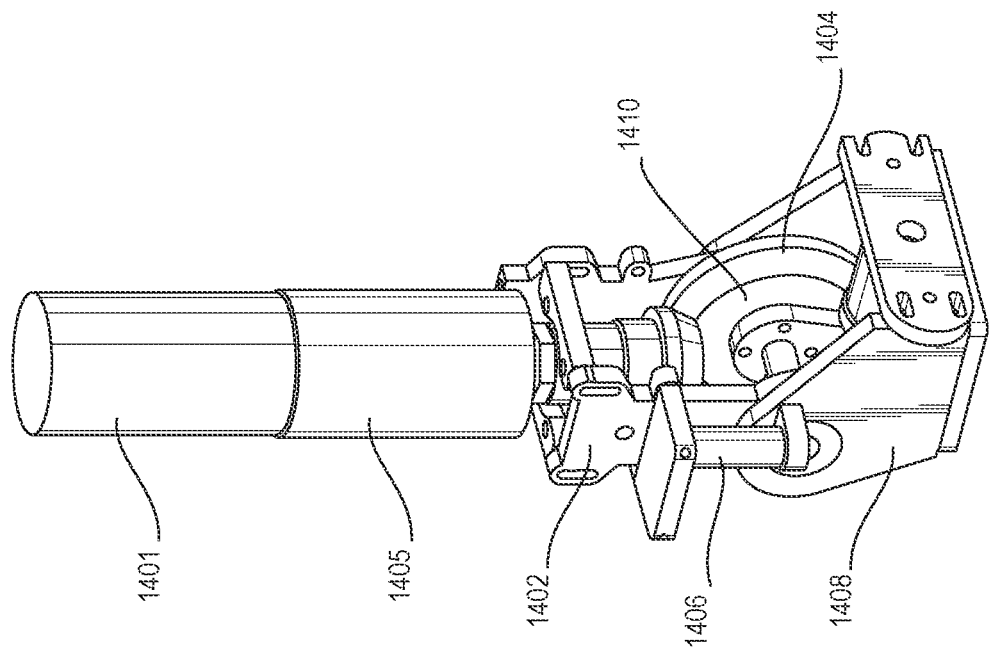
FIG. 14 is a perspective drawing illustrating the physical implementation of the first embodiment of the invention.
Figure 12:
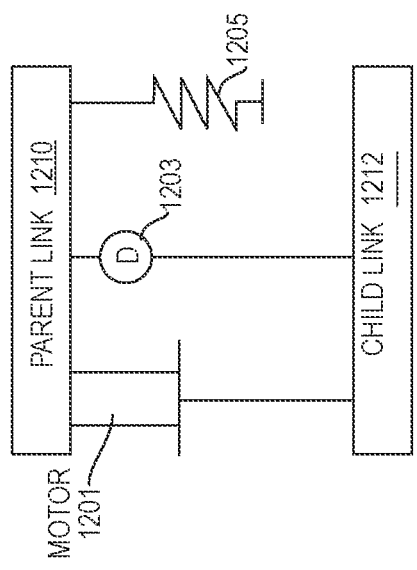
FIG. 12 is a lumped parameter model a first embodiment of the invention forming a biomimetic ankle.
Figure 13:
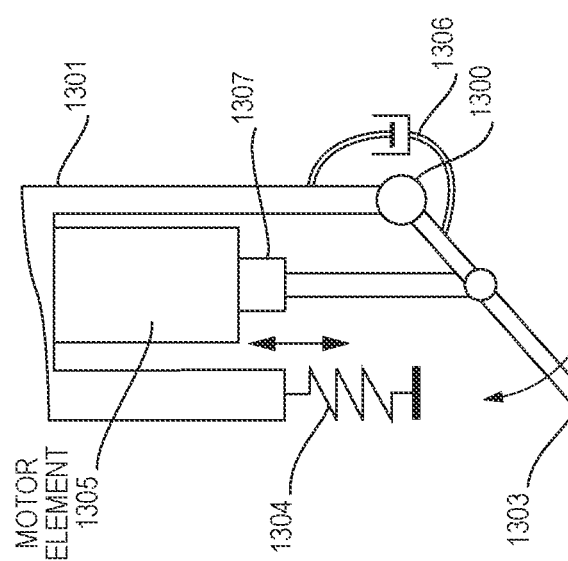
FIG. 13 is a schematic drawing of the first embodiment of the invention.
Figure 16:
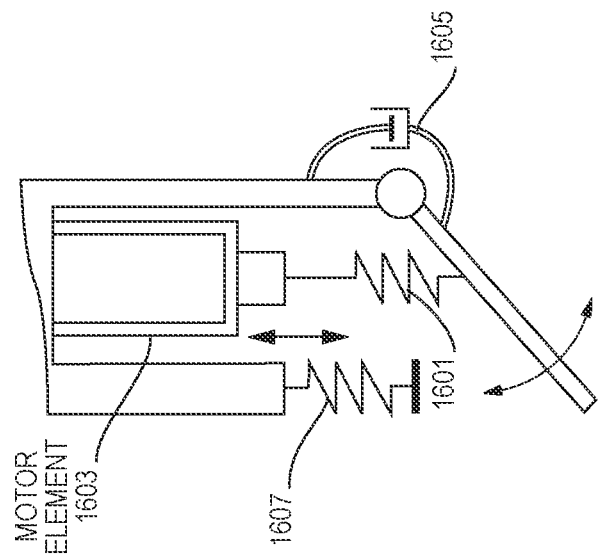
FIG. 16 is a schematic drawing of the second embodiment of the invention.
Figure 15:
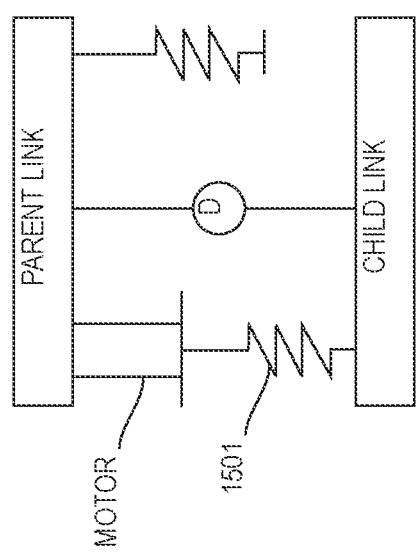
FIG. 15 is a lumped parameter model a second embodiment of the invention forming a biomimetic ankle.

Embodiment 1 is depicted in FIGS. 12-14. As seen in the lumped parameter model of FIG. 12, the first embodiment implements an artificial ankle and comprises a motor 1201 and a global variable damper 1203 to provide control of joint position and mechanical energy absorption rate. In the description that follows, it will be shown how this first embodiment may be used to implement an artificial ankle, with a global one way spring 1205 being placed in parallel with the motor 1201 and the global variable damper 1203 between the parent link 1210 at the shin and a child link 1212 at the foot.

As seen in the schematic diagram of FIG. 13, the first embodiment forms a joint 1300 between the parent link seen 1301 (at the shin shown at 1210 in FIGS. 12 and 1402 in FIG. 14) and a child link 1303 (at the foot link seen at 1212 in FIG. 12 and at 1408 in FIG. 14). An electric motor seen at 1305 (and at 1201 in FIGS. 12 and 1401 in FIG. 14) rotates the foot member 1303 with respect to the shin member 1301 about the joint 1300. A one directional spring element 1304 (also seen at 1205 in FIG. 12 and at 1406 in FIG. 14) arrests the motion of the foot member 1303 when it rotates upwardly (ankle dorsiflexion) beyond a predetermined position toward the shin member 1301. A brake member 1306 (corresponding to the global variable damper seen at 1203 in FIG. 12 and at 1410 in FIG. 14) can be controlled to arrest the rotation of the foot member with respect to the shin member. A gearbox at 1307 (also seen at 1405 in FIG. 14) couples the motor to the foot member 1303 for rotation about the joint 1300.

The physical form of an artificial ankle employing the hybrid actuator is seen in FIG. 14. The electric motor is seen at 1401 attached to a parent link structure 1402 at the shin drives a bevel gear 1404 through a gearbox 1405. A passive extension spring seen at 1406 attached to the parent link 1402 engages the child link attachment 1408 when it rotates upwardly past a predetermined position. A rotary MR damper seen at 1410 acts as a controllable brake.

During level-ground walking, the global variable-damper is set at a high damping level to essentially lock the ankle joint during early to midstance, allowing spring structures within the artificial foot (not shown) to store and release elastic energy. Once body weight has transferred from the heel to the forefoot of the artificial foot, the ankle begins to dorsiflex and the passive extension spring is compressed. In PP, as the loading from the body weight decreases, the extension spring releases its stored elastic energy, rotating in a plantar flexion direction and propelling the body upwards and forwards. After toe-off, the variable damper minimizes joint damping, and the motor controls the position of the foot to achieve foot clearance during the swing phase and to maintain a proper landing orientation of the foot for the next stance period.

From {1} {2}, it has been shown that the maximum dorsiflexion ankle torque during level-ground walking is in the range from 1.5 Nm/kg to 2 Nm/kg, i.e. around 150 Nm to 200 Nm for a 100 kg person. With current technology, a variable-damper that can provide such high damping torque and additionally very low damping levels is difficult to build at a reasonable weight and size. Fortunately, the maximum controlled plantar flexion torque is small, typically in the range of 0.3 Nm/kg to 0.4 Nm/kg. Because of these biomechanics, a uni-directional spring that engages at a small or zero dorsiflexion angle (90 degrees between foot and shank) would lower the peak torque requirements of the active ankle elements (global variable damper and motor) since the peak controlled plantar flexion torque is considerably smaller than the peak dorsiflexion torque.

For ascending a stair or slope, the uni-directional extension spring is immediately engaged because the artificial toe is loaded at first ground contact. After the spring is compressed, the extension spring releases its energy, supplying forward propulsion to the body. The variable damper may be activated to control the process of energy release from the extension spring. After toe-off, the motor controls the equilibrium position of the ankle in preparation for the next step. For slope ascent, the ankle is dorsiflexed at first ground contact to accommodate the angle of the slope. The greater the slope angle or steepness, the more the ankle is dorsiflexed at first ground contact. Here the motor dorsiflexes the ankle during the swing phase, compressing the passive extension spring. Throughout the first half of ground contact, the spring is compressed farther, and then all the stored spring energy is released during powered plantar flexion throughout the latter half of ground contact, powering uphill progression.

During stair descent, the body has to be lowered after forefoot contact until the heel makes contact with the stair tread {2}. Since the motor is in parallel with the variable damper, negative work can be performed by both the variable damper and the motor. Here the damper dissipates mechanical energy as heat, and the motor acts as a generator, converting mechanical energy into electrical energy. Once the foot becomes flat on the ground, the uni-directional extension spring becomes engaged, storing energy as the artificial ankle dorsiflexes. During PP, the extension spring releases its energy, propelling the body upwards and forwards. For slope descent, the ankle response is similar, except that mechanical energy is absorbed by the variable damper and motor during controlled plantar flexion instead of during controlled dorsiflexion.

Embodiment 2

Mechanical Design

Embodiment 2 is shown in FIGS. 15-18. As seen by a comparison of the lumped parameter models seen in FIGS. 12 and 15, and also comparing the schematic drawings of FIGS. 13 and 16, it may be seen that the second embodiment includes an additional "motor series spring" element seen at 1501 in FIG. 15, at 1601 in FIG. 16, and at 1711 in FIGS. 17 and 18. In addition to the capabilities offered by Embodiment 1, Embodiment 2 provides for the control of hybrid actuator force by an active spring deflection control by the motor and an active damping control by the variable damper. In addition, Embodiment 2 includes the capacity to act as a catapult where a spring is slowly compressed and that stored potential energy is used all at once at a later time. For the catapult control, the global variable-damper 1605 will be able to control the damping of the joint in order to modulate how much energy is actually released from the stored catapult energy. In the section to follow, we provide an example of how the hybrid biomimetic actuator of Embodiment 2 can be employed as an artificial ankle.

Figure 18:
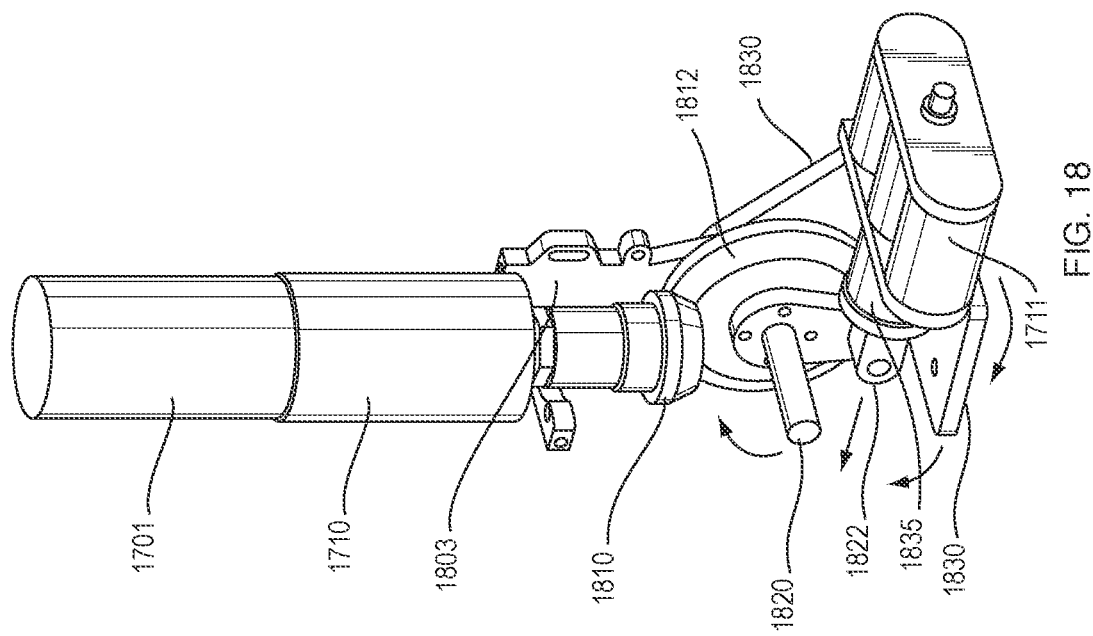
FIGS. 17 and 18 are two perspective drawings illustrating the physical implementation of the second embodiment of the invention.
Figure 17:
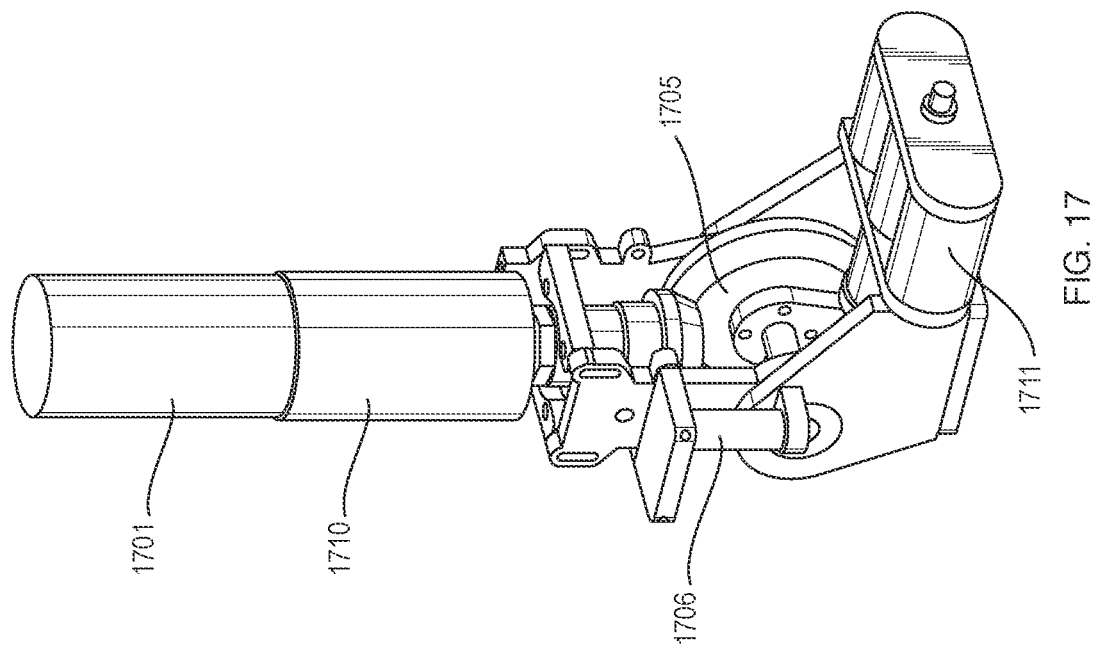

As seen in FIGS. 17 and 18, the second embodiment includes an electric motor seen at 1701 (and at 1603 in FIG. 16) in parallel with a rotary magnetorheological (MR) variable-damper 1705 (1605 in FIG. 16) where the MR fluid is used in the shear mode. Similar to Embodiment 1 as seen in FIG. 14, the uni-directional spring, the passive extension spring at 1706 (1607 in FIG. 16), is engaged for ankle angles of 90 degrees or less (dorsiflexion). For angles greater than 90 degrees (plantar flexion), the spring is no longer engaged, and the ankle joint freely rotates without spring compression. As best seen in FIG. 18, a drive shaft 1803 links the motor 1701, a gearbox 1710, and motor series springs seen at 1711. Torque is transmitted from motor 1701 through gearbox 1710, to bevel pinion seen at 1810. This gear transfers torque to the large bevel gear at 1812. The rotational motion of the large bevel gear is converted to linear motion at the joint at 1820 by the spring pivot rod 1822 which compresses extension series springs at 1711. The other end of the extension series spring pushes on the structure that is rigidly attached to the child link 1830. For flexion, the direction of rotation of the motor is reversed, and the torque to the child link is transmitted via the flexion series springs seen at 1835.

The second embodiment, like the first embodiment described earlier, includes a uni-directional global spring (seen at 1205, 1304 and 1406 in the first embodiment and at 1706 in FIG. 17) that provides passive spring operation throughout ankle dorsiflexion. However, in distinction to Embodiment 1, the Embodiment 2 artificial ankle further includes the flexion series spring 1835 to provide powered plantar flexion during the terminal stance period.

One of the main challenges in the design of an artificial ankle is to have a relatively low-mass actuation system, which can provide a large instantaneous output power upwards of 200 watts during powered plantar flexion (PP) {1} {2}. Fortunately, the duration of PP is only 15% of the entire gait cycle, and the average power output of the human ankle during the stance phase is much lower than the instantaneous output power during PP. Hence, a catapult mechanism is a compelling solution to this problem.

The catapult mechanism is mainly composed of three components: the motor 1701, the variable damper 1705 and/or clutch and an energy storage element such as the springs 1711. With the parallel damper activated to a high damping level or with the parallel clutch activated, the series elastic element (e.g. the motor spring seen at 1501, 1601 and 1711) can be compressed or stretched by the motor in series with the spring without the joint rotating. The spring will provide a large amount of instantaneous output power once the parallel damping device or clutch is deactivated, allowing the elastic element to release its energy. If the motor has a relatively long period of time to compress or stretch the elastic element, its mass can be kept relatively low, decreasing the overall weight of the artificial ankle device. In the ankle system of Embodiment 2, the catapult system comprises a magnetorheological variable damper (seen at 1203, 1306, and 1410 in the drawings of the first embodiment and at 1705 in FIG. 17) placed in parallel to a motor and a motor series spring.

During the CP phase of level-ground walking, the motor controls the stiffness of the ankle by controlling the displacement of the series flexion springs seen at 1835 in FIG. 18. During CD, the series extension springs at 1711 then compress due to the loading of body weight, while the actuator additionally compresses the series springs to store additional elastic energy in the system. In this control scheme, inertia and body weight hold the joint in a dorsiflexed posture, enabling the motor to further compress the series extension springs. In a second control approach, where body weight and inertia are insufficient to lock the joint, the MR variable damper would output a high damping value to essentially lock the ankle joint while the motor stores elastic energy in the series springs. Independent of the catapult control approach, during PP, as the load from body weight decreases, the series extension springs begin releasing stored elastic energy, supplying high ankle output powers during PP. The variable damper is significant in the synchronization of the energy relaxation from the series extension springs. After toe-off, the actuator controls the position of the ankle to achieve foot clearance and a proper landing orientation for the next stance period.

Embodiment 3

Mechanical Design

Embodiment 3 is shown in FIGS. 19-21 and also comprises a motor, a motor series spring, and a variable damper in parallel with the motor as seen in FIG. 19. The third embodiment differs from the second in that the variable damper is connected to retard motor motion. In addition to the capabilities offered by Embodiment 1, Embodiment 3 provides for low-power spring stiffness and spring equilibrium point control.

Usage Example for Embodiment 3

The mechanical design and the corresponding schematic for Embodiment 3, as used for an artificial ankle application, are shown in FIGS. 20 and 21. Similar to the ankle designs corresponding to Embodiments 1 and 2, a uni-directional global spring (seen at 1205, 1304 and 1406 for the first embodiment) provides for a passive spring operation throughout ankle dorsiflexion. However, in distinction to Embodiments 1 and 2, the Embodiment 3 artificial ankle is capable of controlling ankle joint spring stiffness and equilibrium at low electrical power requirements.

FIG. 21 provides a perspective view of Embodiment 3 used as an artificial ankle system. The ankle design includes an electric motor 2110, a gearbox 2111 (2009 in FIG. 20), a bevel gear 2109, and a motor series spring 2120. In parallel with the motor is a rotary hysteresis variable-damper 2125 in FIG. 21. Similar to the ankle of Embodiments 1 and 2, the uni-directional spring seen at 2140 in FIG. 21 is engaged for ankle angles of 90 degrees or less (dorsiflexion). For angles greater than 90 degrees (plantar flexion), the spring 2140 is no longer engaged, and the ankle joint freely rotates without spring compression. The ankle joint seen at 2000 in FIG. 20 is seen at 2142 in FIG. 21 rotates child foot member 2155 (2013 in FIG. 20) with respect to the parent shin member 2160 (2014 in FIG. 20).

There are separate series springs at 2120 and 2150 for extension and flexion respectively, and these two sets of springs can be selected to give distinct flexion and extension joint stiffnesses. If the motor changes ankle position when minimal torques are applied to the joint, such as during the swing phase of walking, very little electrical power is required to change the spring equilibrium position of the joint. Just before the joint is loaded by body weight at heel strike, the motor parallel variable damper can be locked, with relatively low electrical power required, so that the motor need not consume electrical power to hold the joint's position. Changing this spring joint set point can be useful, for example, when the wearer switches shoes with different heel heights, thus changing the natural angle of the ankle joint when the foot is resting on a flat ground surface.

The variable damper and motor can also act to modulate the quasi-stiffness of the ankle joint at low electrical power requirements. Here quasi-stiffness refers to the slope of the ankle torque versus position curve. If the series springs 2120 and 2150 are set to maximal stiffness levels demanded by the application, and the damper and motor are controlled to absorb mechanical energy by backing off the opposite end of the spring as the spring is being compressed by torques applied to the joint, the effective stiffness of the ankle joint can be controlled. This system can directly control stiffness at low power, since the variable damper is attached before the motor's gear reduction, so that the damper rotates at high angular velocity but at low torque output relative to the joint being controlled.

To generate high output mechanical powers during PP in walking, the body's weight and inertia can act as a "clutch" to essentially lock the ankle joint in a catapult mode control, so that as the body rotates above the stance foot, the motor can be steadily "winding up" its series extension springs in order to release that energy later during the PP phase. During this "winding up" control period, joint torque can be directly controlled by controlling series spring compression using feedback of series spring deflection.

Similar to Embodiments 1 and 2, Embodiment 3 can also share the load of absorbing energy between the motor and the variable damper. This may cut down on heat generated by the variable damper under heavy use, and the electric motor can act regeneratively, generating electrical power and thus increasing overall efficiency. For example, in the case of walking down hill, it is important for the biomimetic ankle joint to absorb mechanical energy in order to smooth and cushion descent. This energy absorption can be achieved by allowing the motor to back drive and the variable damper to dissipate the energy in a controlled, modulated way, depending on the mass of the person, how fast they are walking, and how steep the descent may be. Here again, the motor can share the mechanical energy absorption with the parallel variable damper, generating electrical power in the process. It is noted here that back driving a motor of reasonable size and weight will not, by itself, absorb a sufficient amount of mechanical energy for this particular application, and that both motor and variable damper must therefore share in the power absorption.

Embodiment 4

Mechanical Design

Figure 24:
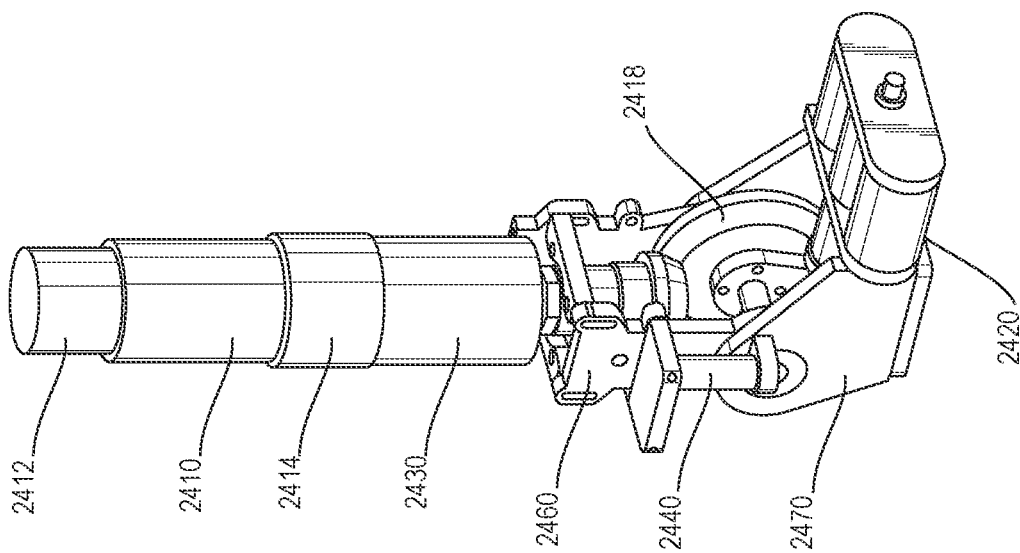
FIG. 24 is a perspective drawing illustrating the physical implementation of the fourth embodiment of the invention.
Figure 22:
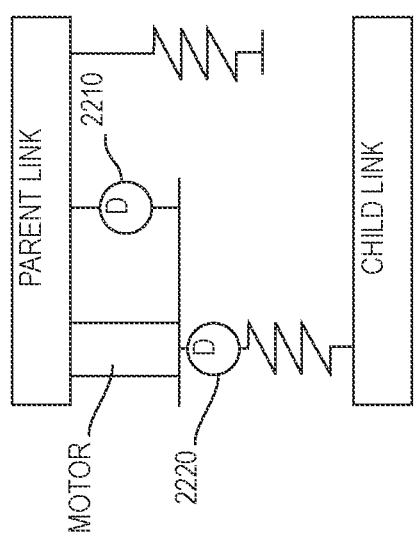
FIG. 22 is a lumped parameter model a fourth embodiment of the invention, a biomimetic ankle.
Figure 23:
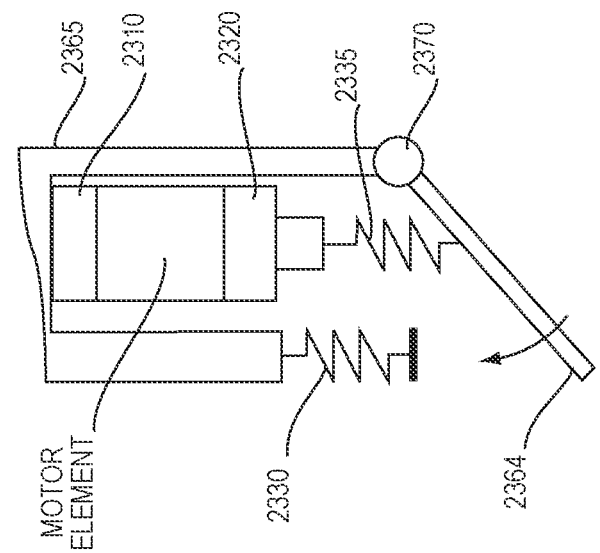
FIG. 23 is a schematic drawing of the fourth embodiment of the invention.

Embodiment 4, shown in FIGS. 22-24, comprises a motor, a motor series spring, a motor parallel variable damper seen at 2210 in FIG. 22, at 2310 in FIG. 23, and at 2412 in FIG. 24. A motor series variable damper is seen at 2220 in FIG. 22, at 2320 in FIG. 23, and at 2414 in FIG. 24. In addition to the capabilities offered by Embodiment 3, Embodiment 4 allows the actuator to be back driven very easily for tasks where hybrid actuator force needs to be minimized at minimal energy demands from the power supply. The addition of the motor series variable damper allows the gearbox to freewheel at high angular rates without the need for the motor to slew as well, lowering the minimal force output of the biomimetic actuator at minimal power input requirements. In the case of Embodiment 3 where no motor series variable damper exists, when the actuator is compressed passively, consuming zero energy from the power supply, the motor and the parallel variable damper both have to rotate. In distinction, with the Embodiment 4 architecture, when the motor parallel variable damper outputs high damping, locking the motor, only the motor series variable damper rotates when the actuator is compressed. Since the motor series variable damper is before the mechanical transmission, the damper can be relatively small with a negligible passive, zero-energy damping torque, and thus the mechanical transmission itself will be the only dominant source of passive actuator resistance or inertia under compression, resulting in a biomimetic joint that can go more limp or slack while requiring only minimal energy from the power supply. The child foot link at 2364 rotates with respect to the parent shin link at 2365 rotates about the joint is seen at 2370.

Embodiment 4, as seen in FIG. 24, includes an electric motor 2410 and motor series springs at 2420 (2335 in FIG. 23) for joint flexion and extension. The motor 2410 drives the bevel gear 2418 to compress the series springs 2420. In parallel and in series with the motor are rotary hysteresis variable-dampers. The hysteresis brake seen at 2412 in FIG. 24 arrests the motion of the motor 2410. The second hysteresis brake is seen at 2414 and is operatively connected between the motor 2410 and the gearbox 2430. Similar to the three ankle embodiments described above, the unidirectional spring, shown at 2440, and at 2330 in FIG. 23, is engaged for ankle angles of 90 degrees or less (dorsiflexion). For angles greater than 90 degrees (plantar flexion), the spring is no longer engaged, and the ankle joint freely rotates without spring compression. The parent shin link structure is seen at 2460 and the child foot structure is seen at 2470.

In addition to improving the low-energy, minimum force capabilities of the actuator, the actuator of Embodiment 4 can dissipate mechanical energy without back driving the motor by once again using the motor parallel variable damper 2412 to lock the motor rotor at low energy demands from the power supply. Although controlling the actuator in this manner eliminates the opportunity to employ the motor as a generator, it is beneficial in that it will result in a quieter biomimetic actuator operation. Since it is important that robots, prostheses and orthoses be quiet, this engineering tradeoff is often worthwhile. An example of the use of Embodiment 4 as an artificial ankle is provided in the next section.

Usage Example for Embodiment 4

In comparison with the previous ankle embodiments, the Embodiment 4 artificial ankle has a quieter operation and a lower output force while requiring minimal energy demands from the power supply. Since the motor will not be rotating while mechanical energy is being absorbed by the motor series damper, the force output of the system will be lowered, resulting in an ankle joint that can go more limp or slack while consuming only that energy required to output sufficiently high damping in the motor parallel variable damper to lock the rotor of the motor. In addition, this actuator feature reduces the level of noise from the actuator during mechanical energy absorption since no noise will result from back driving the motor. The motor series damper could also be used to modulate the force output of the series springs in a quiet and efficient manner as they discharge their energy after being "wound up" in a catapult mode. In addition to these distinct features, the ankle corresponding to Embodiment 4 offers the same capabilities as the ankle system of Embodiment 3.

Embodiment 5

Mechanical Design

Figure 27:
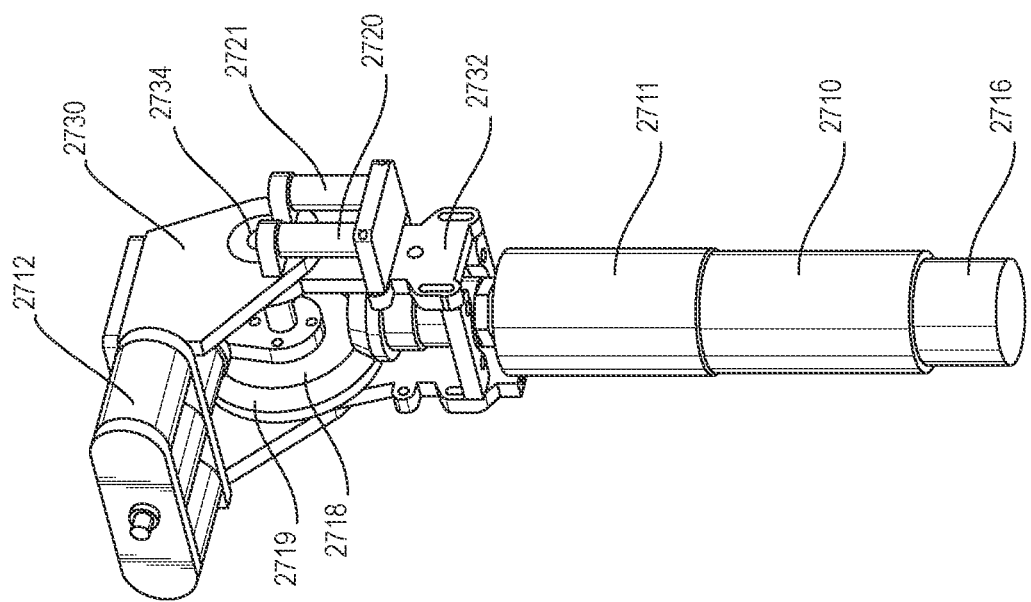
FIG. 27 is a perspective drawing illustrating the physical implementation of the fifth embodiment of the invention.
Figure 25:
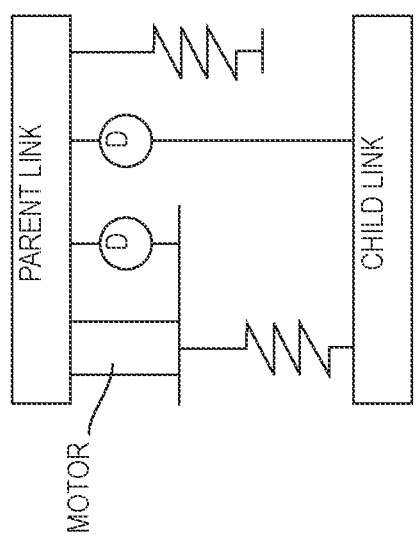
FIG. 25 is a lumped parameter model a fifth embodiment of the invention, a biomimetic knee.
Figure 26:
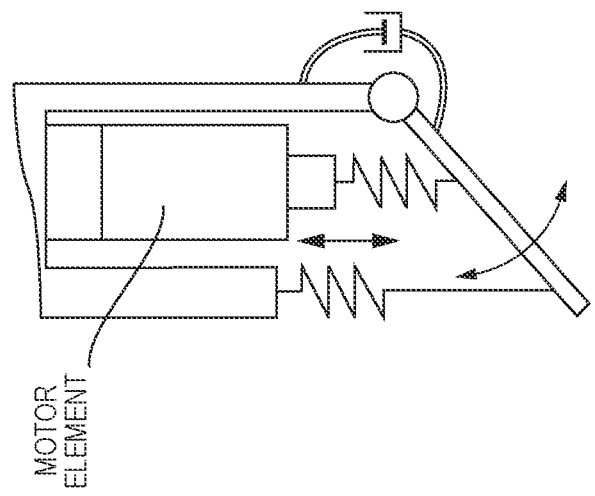
FIG. 26 is a schematic drawing of the fifth embodiment of the invention.

Embodiment 5 is a biomimetic hybrid knee shown FIGS. 25-27. As shown in the perspective drawing, FIG. 27, five elements are included in the design: a motor 2710, a gearbox 2711, a bevel gear 2719, a motor series coil springs for joint flexion and extension seen at 2712, a motor parallel variable-damper 2716, a global variable damper 2718, and a bi-directional spring that consists of a light extension spring 2720 and a stiff kneecap spring 2721. The global damper 2718 and the motor-parallel variable damper 2716 are rotary magnetorheological (MR) and hysteresis variable-dampers, respectively. To resist knee hyperextension, the stiff kneecap flexion spring 2721 serves as an artificial knee cap stop. In addition, the light extension spring 2720 is included to bias the knee towards a fully extended posture. The structure rotates the child thigh member at 2730 with respect to the parent thigh structure at 2732 about the joint 2734.

In addition to the capabilities offered by Embodiment 3, the BHA of Embodiment 5 allows the joint to act as a "catapult" at any time in its operation. The addition of the global variable damper 2718 allows the joint to be locked while the motor 2710 slowly compresses the series springs 2712, and that stored potential energy can then be used all at once at a later time. To release the stored elastic energy, the output damping from the global damper 2718 is minimized, unlocking the actuator and releasing the energy. Also, the global variable-damper 2718 of Embodiment 5 will be able to directly modulate the damping of the actuator in order to control how much energy is actually released to the external world from the stored catapult energy. An example of the use of Embodiment 5 as an artificial knee is provided in the next section.

Usage Example for Embodiment 5

Figure 5:
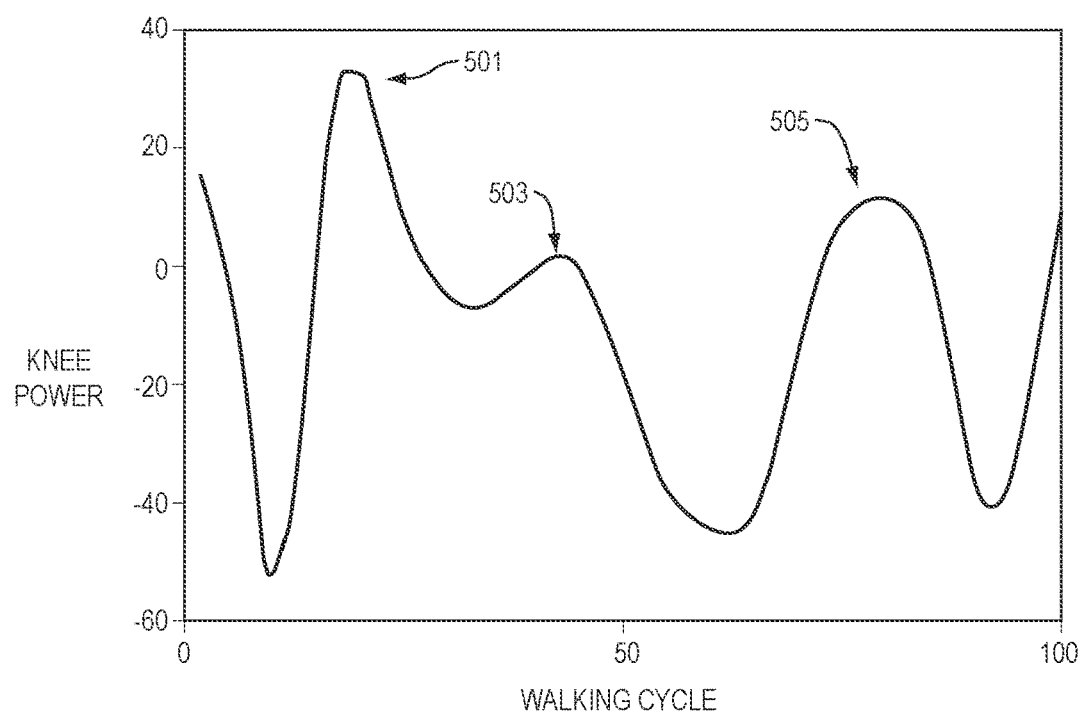

State of the art commercially available knee prostheses employ a global variable damper and a global two-way spring {5}. Consequently, current knee prostheses cannot control knee position when the foot is off the ground, and are incapable of generating net positive work and power during stance or swing. As shown in FIG. 5, the human knee has three positive power contributions (seen at 501, 503 and 505) throughout the walking gait cycle. Because conventional prosthetic knees only have a global variable damper and a low stiffness global spring, these positive power contributions cannot be achieved.

The artificial knee corresponding to Embodiment 5 improves upon these contemporary prosthetic knee designs by placing a motor, a motor parallel variable damper, and a motor series spring all in parallel with the conventional global damper/spring. During early stance knee flexion in level-ground walking, energy in the knee can be dissipated with the global variable damper as is typically done with conventional artificial knee systems. However, during stance knee extension, the motor parallel variable damper 2716 can be locked as the hip joint actively extends, rotating the thigh rearwardly. This movement allows energy from hip muscular work to be stored in the series flexion springs 2712 located in the knee assembly. The stored elastic energy can then be released during early pre-swing to help flex the knee during terminal stance in preparation for the swing phase. This positive power burst corresponds to 503 in FIG. 5. The global damper can be used to modulate the actual external power generated from the spring energy. It is worth noting again that this method allows the hip muscles to store energy in the knee as the stance leg is rotated rearwardly during hip extension, and that this energy can be reused at a later time to help flex the knee with very little energy required from the artificial knee's power supply.

Once the elastic energy from the series flexion springs has been released and the artificial leg has entered the swing phase, the knee joint has to absorb mechanical energy to decelerate the swinging lower leg. To this end, during late swing flexion, the motor parallel variable damper 2716 can lock once again, causing the series extension springs 2712 in the knee assembly to deflect and store energy. This stored energy can then be using to create positive power burst at 505 (FIG. 5) during the early swing extension period, requiring, once again, very little energy from the knee's power supply. In all cases, the global variable damper can be used to precisely modulate the amount of power delivered to the swinging artificial leg from energies storied in the series springs. Further, the global variable damper can dissipate kinetic energy from the swinging leg to achieve the large negative powers during the swing phase (see FIG. 5).

In summary, the artificial knee corresponding to Embodiment 5 is capable of reproducing the positive power contributions 503 and 505 shown in FIG. 5. Both positive power contributions 501 and 503 cannot be achieved by the architecture of Embodiment 5. However, Embodiment 7 described below is capable of capturing all three positive power contributions.

For stair/slope descent, the global variable damper, motor and motor parallel variable damper can all be used to dampen the knee joint and to absorb mechanical energy for a prosthetic/orthotic knee wearer or humanoid robot. Although the variable dampers of the hybrid actuator dissipate mechanical energy as heat during the period of stance knee flexion, the motor can act as a generator, storing up electrical energy to be used at a later time. Through mid to terminal stance, the motor parallel variable damper 2716 can then output a high damping value that essentially locks the rotor of the motor, causing the motor series spring 2712 to store energy as the artificial knee undergoes terminal flexion. This stored energy can then be used during the swing phase to promote knee extension to prepare the artificial leg for the next stance period.

For stair/slope ascent, during the swing phase the motor can actively control knee position to accurately locate the foot on the next stair tread or slope foothold. Once the artificial foot is securely positioned on the ground, the motor can then deflect and store energy in the motor series extension springs. This stored elastic energy can then assist the knee wearer or humanoid robot to actively straighten the knee during the stance period, lifting the body upwards.

Finally, Embodiment 5 allows for the "windup" phase of the catapult style control to occur at any desired time, as opposed to embodiment 3, which requires an inertial clutch (body mass during stance phase for ankle joint for example). This means much greater flexibility as to when large amounts of power can be efficiently generated and used. This flexibility is critical when designing an artificial knee that can be used for jumping. For such a movement task, energy has to be stored prior to the jump, and then the elastic energy has to be released at a precise time to facilitate a jumping action.

Embodiment 6

Mechanical Design

Figure 30:
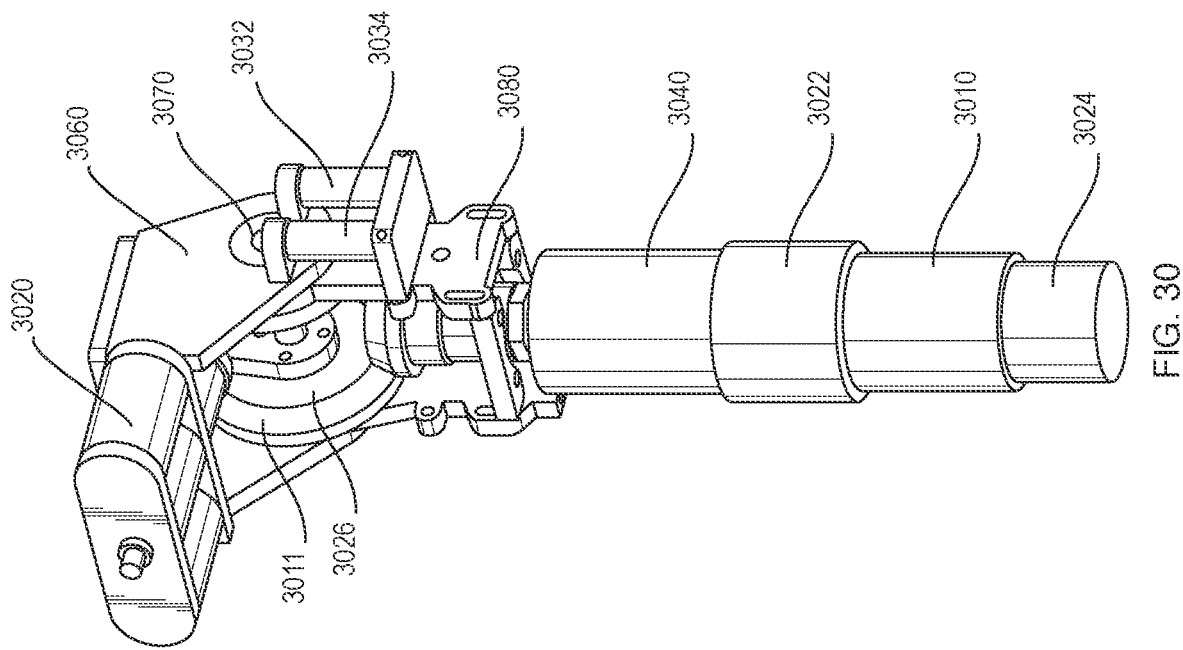
FIG. 30 is a perspective drawing illustrating the physical implementation of the sixth embodiment of the invention.
Figure 28:
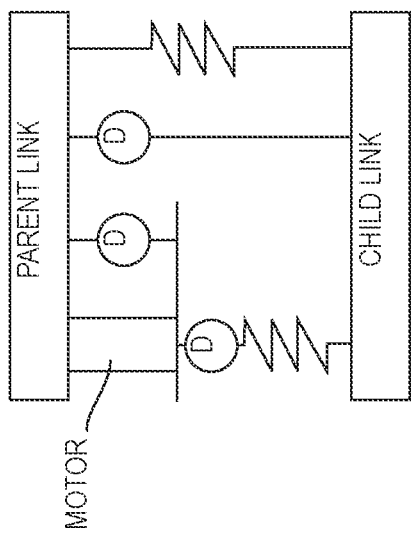
FIG. 28 is a lumped parameter model a sixth embodiment of the invention, a biomimetic knee.
Figure 29:
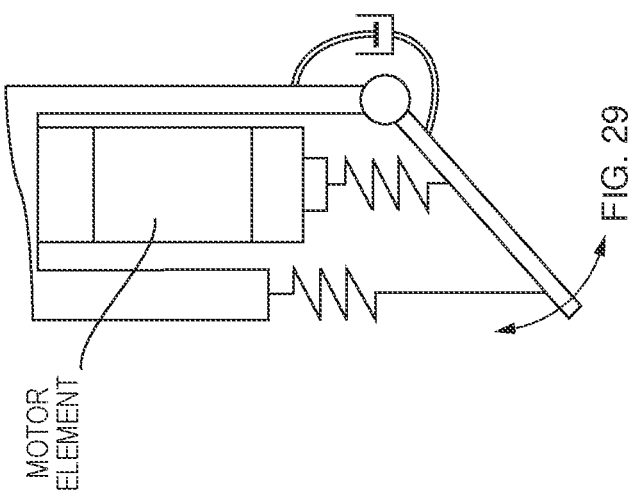
FIG. 29 is a schematic drawing of the sixth embodiment of the invention.

Embodiment 6, a biomimetic knee employing a Biomimetic Hybrid Actuator, is shown in FIGS. 28-30. The elements included in the design as shown in FIG. 30: a motor 3010, a bevel gear 3011, a motor series spring 3020 for joint flexion and extension, a motor series variable damper 3022, a motor parallel variable-damper 3024, a gearbox 3040, a global variable damper 3026, and a bi-directional spring assembly consisting of a stiff kneecap flexion spring 3032 and a light extension spring 3034. The two dampers 3022 and 3024 are hysteresis brakes, and global damper 3026 is a rotary magnetorheological (MR) variable-damper technology in which the MR fluid is used in the shear mode. To resist knee hyperextension, the stiff kneecap flexion spring 3032 serves as an artificial knee cap stop. In addition, the light extension spring 3034 is included in the design to bias the knee towards a fully extended posture. The thigh (child link) structure at 3060 supports the axis of the joint at 3070 about which the shin (parent link) structure 3080 rotates.

In addition to the capabilities offered by Embodiment 5, Embodiment 6 allows the actuator to be back driven very easily for tasks where the hybrid actuator force needs to be minimized at minimal energy demands from the power supply. The addition of the motor series variable damper 3022 allows the gearbox to freewheel at high angular rates without the need for the motor to slew as well, lowering the minimal force output of the biomimetic actuator at minimal power input requirements. In the case of Embodiment 5 where no motor series variable damper exists, when the actuator is compressed passively, consuming zero energy from the actuator power supply, the motor and the parallel variable damper both have to rotate or compress. In distinction, with the Embodiment 6 architecture, when the motor parallel variable damper 3024 outputs high damping, locking the motor, only the motor series variable damper 3022 rotates or compresses when the actuator is compressed. Since the motor series variable damper 3022 is placed before the mechanical transmission including a gearbox 3040, the damper 3022 can be relatively small with a negligible passive, zero-energy damping torque, and thus the mechanical transmission including the gearbox 3040 and the global variable damper 3026 will be the only dominant sources of passive actuator resistance under compression, resulting in a biomimetic actuator that can go more limp or slack while requiring only minimal energy from the power supply.

In addition to improving the low-energy, minimum force capabilities of the actuator, the actuator of Embodiment 6 can dissipate mechanical energy without back driving the motor by once again using the motor parallel variable damper to lock the motor rotor at low energy demands from the power supply. Although controlling the actuator in this manner eliminates the opportunity to employ the motor as a generator, it may be beneficial in that it will result in a quieter biomimetic actuator operation. Since it is often important that robots, prostheses and orthoses are quiet, this engineering tradeoff may be selected for many applications. An example of the use of Embodiment 6 of the Biomimetic Hybrid Actuator to implement an artificial knee (Embodiment 10) is provided in the next section.

Usage Example for Embodiment 6

Similar to the knee design corresponding to Embodiment 5, a bi-directional global springs 3032 and 3034 provides for a passive extension spring operation to bias the knee towards a fully extended posture (spring 3034), and a stiff flexion spring operation (spring 3032) to limit the knee's movement so that knee hyperextension cannot occur. However, in distinction to the previous knee embodiment, the Embodiment 6 artificial knee has a quieter operation and a lower output force while requiring minimal energy demands from the power supply.

Since the motor will not be rotating while mechanical energy is being absorbed by the motor series and global variable dampers, the force output of the system will be lowered, resulting in a knee joint that can go more limp or slack while consuming only that energy required to output sufficiently high damping in the motor parallel variable damper 3024 to lock the rotor of the motor. In addition, this actuator feature reduces the level of noise from the actuator during mechanical energy absorption since no noise will result from back driving the motor. The motor series damper 3022 could also be used to modulate the force output of the series springs in a quiet and efficient manner as they discharge their energy after being "wound up" in a catapult mode. Further, the global variable damper can dissipate kinetic energy from the swinging leg to achieve the large negative powers during the swing phase (see FIG. 5). In addition to these distinct features, the knee corresponding to Embodiment 6 offers the same capabilities as the knee system of Embodiment 5.

Embodiment 7

Mechanical Design

Figure 33:
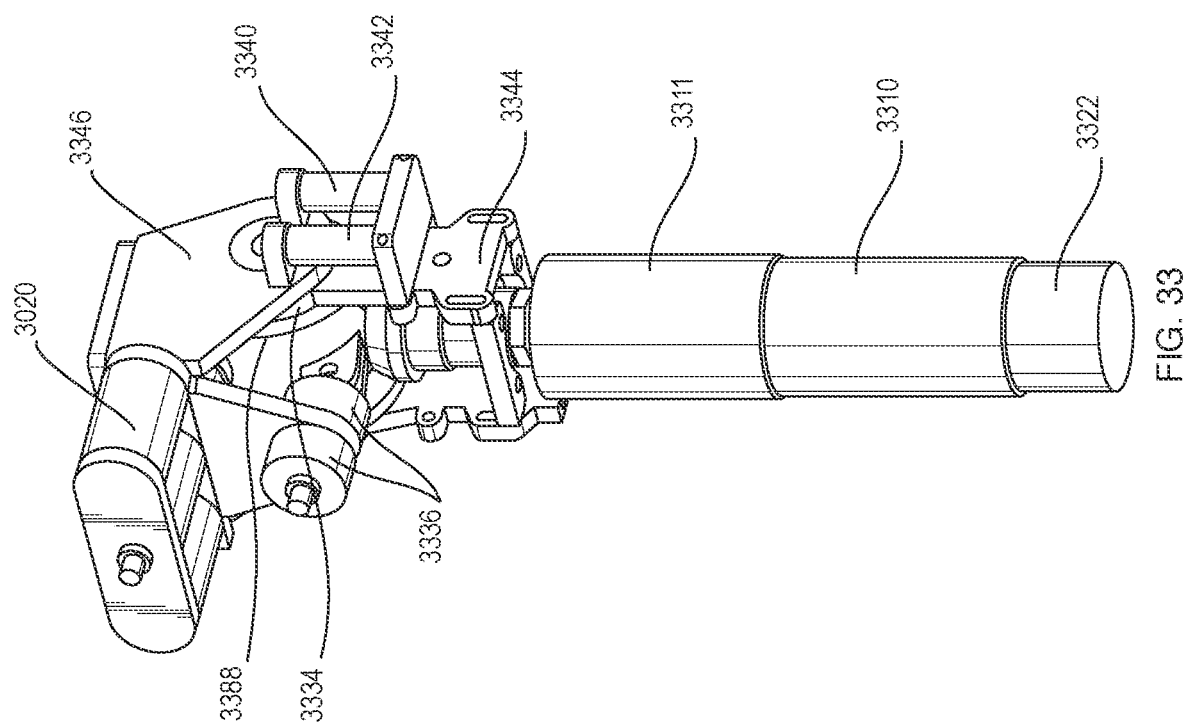
FIG. 33 is a perspective drawing illustrating the physical implementation of the seventh embodiment of the invention.
Figure 31:
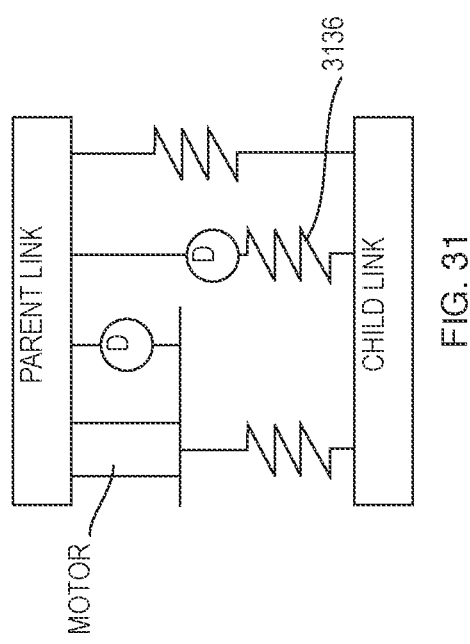
FIG. 31 is a lumped parameter model a seventh embodiment of the invention, a biomimetic ankle.
Figure 32:
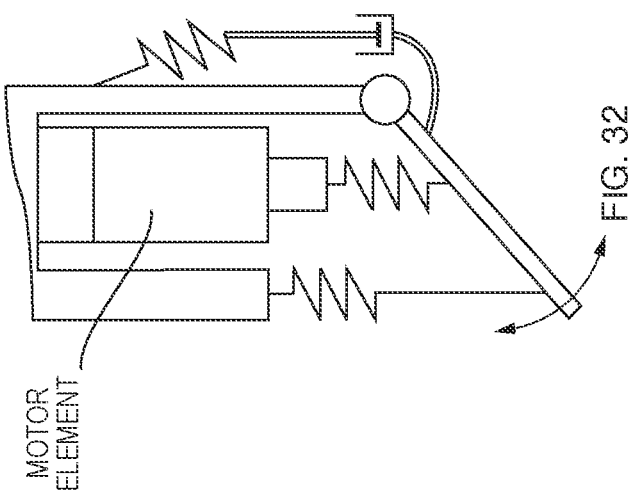
FIG. 32 is a schematic drawing of the seventh embodiment of the invention.

A biomimetic hybrid knee design corresponding to Embodiment 7 is shown in FIGS. 31-33. Six elements are included in the design as seen in FIG. 33: a motor 3310, a gearbox 3311, a motor series spring 3320 for joint flexion and extension, a motor parallel variable-damper 3322, a global variable damper 3334, a bi-directional global spring comprising a stiff spring 3340 and a light extension spring 3342, and a global damper spring 3336 also seen at 3136 in FIG. 31. The motor drives the joint via a bevel gear at 3388 to rotate the parent (shin) structure 3344 with respect to the child (thigh) structure 3346. The global variable damper 3334 is a magnetorheological (MR) variable-damper, and the motor-parallel variable damper 3322 is a hysteresis brake. The global damper coil springs 3336 (Series Damper Springs) are included for joint flexion and extension. To resist knee hyperextension, the stiff kneecap flexion spring 3340 serves as an artificial kneecap stop. In addition, the light extension spring 3342 is included in the design to bias the knee towards a fully extended posture.

Embodiment 7 allows for the engagement of a second series spring, the damper series spring 3336, at any time during system operation. Further, the energy released from the damper series spring 3336 can be modulated using the global variable damper 3334. An example of the use of Embodiment 7 as an artificial knee is provided in the next section.

Usage Example for Embodiment 7

As shown in FIG. 5, during level-ground walking the human knee has three positive power contributions (seen at 501, 503 and 505). Because conventional prosthetic knees only have a global variable damper and a low stiffness global spring, these positive power contributions cannot be achieved {5}.

The artificial knee corresponding to Embodiment 7 improves upon such contemporary knee designs. During early stance knee flexion in level-ground walking, the global variable damper 3334 can output a high damping value such that as the knee flexes, the global damper spring 3336 stores energy, and then that energy can be released during the stance extension period. This positive power burst corresponds to 501 in FIG. 5. As the stored energy from the global damper spring is being released during stance knee extension, the motor parallel variable damper 3322 can be locked, allowing the energy from hip muscular work and the stored energy in the global damper spring to be stored in the motor series flexion springs 3020 located in the knee assembly. The stored elastic energy can then be released during early pre-swing to help flex the knee during terminal stance in preparation for the swing phase. This positive power burst corresponds to 503 in FIG. 5. During this process, the global damper 3334 can be used to modulate the amount of stored elastic energy in the global damper spring 3336 that is actually released to power the knee joint. In addition, the global variable damper can dissipate kinetic energy from the swinging leg to achieve the large negative powers during the swing phase (see FIG. 5). Still further, the motor parallel variable damper 3322 can be used to modulate the amount of stored elastic energy in the motor series springs 3020 that is actually released to power the knee joint.

Once the elastic energy from the springs 3020 has been released and the artificial leg has entered the swing phase, the knee joint has to absorb mechanical energy to decelerate the swinging lower leg. To this end, during late swing flexion, the motor parallel variable damper 3320 can lock once again, causing the series extension springs 3020 in the knee assembly to deflect and store energy. This stored energy can then be using to create positive power burst seen at 505 in FIG. 5 during the early swing extension period, requiring, once again, very little energy from the knee's power supply.

In all cases, the variable dampers 3322 and 3334 can be used to precisely modulate the amount of power delivered to swinging artificial leg from stored elastic energies. In summary, the artificial knee corresponding to Embodiment 7 is capable of reproducing the three positive power contributions seen at 501, 503 and 505 in FIG. 5 for level-ground walking For stair/slope descent and ascent and for catapult jumping actions, the artificial knee of Embodiment 7 is controlled in a similar manner to that of Embodiment 5.

Embodiment 8

Mechanical Design

Figure 36:
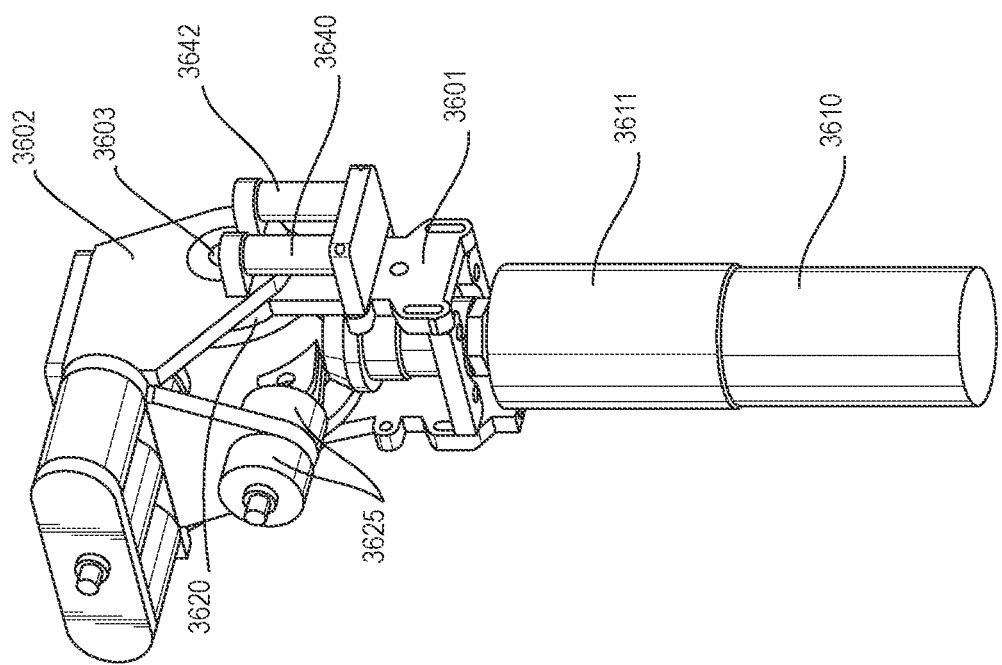
FIG. 36 is a perspective drawing illustrating the physical implementation of the eighth embodiment of the invention.
Figure 34:
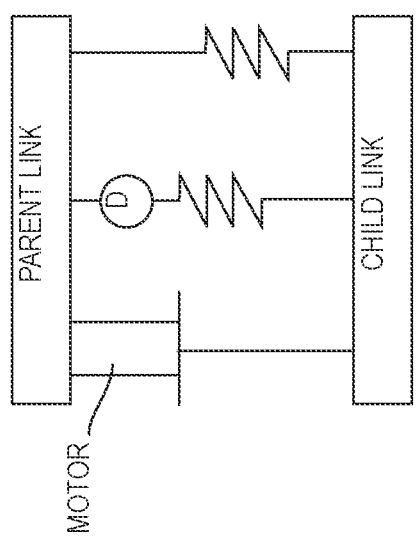
FIG. 34 is a lumped parameter model an eighth embodiment of the invention, a biomimetic hip.
Figure 35:
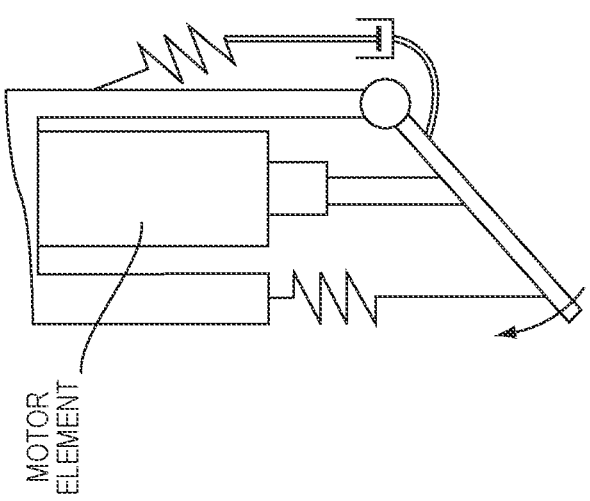
FIG. 35 is a schematic drawing of the eighth embodiment of the invention.

Embodiment 8 is an artificial hip employing a Biomimetic Hybrid Actuator and is shown in FIGS. 34-36. In the artificial hip, the "parent link" seen at 3601 corresponds to the thigh and the "child link" (which in the case of hip joint is above the parent link) at 3602 corresponds to the pelvis. The pelvis structure 3602 supports the axis of the joint at 3603 about which the thigh structure 3601 rotates. The elements included in the design as seen in FIG. 36 are: an electric motor 3610, a gearbox 3611, a global variable MR shear mode damper 3620, a global damper spring 3625, and a bi-directional global spring consisting of a passive flexion spring 3640 and a passive extension spring 3642. The global damper coil springs 3625 are included for joint flexion and extension. Finally, the two-way global springs 3640 and 3642 are included in the design to augment uphill locomotion.

In addition to the capabilities offered by Embodiment 1, Embodiment 8 allows for the engagement of a second series spring, the damper series spring 3625, at any time during system operation. Further, the amount of energy stored or released from the damper series spring 3625 can be modulated using the global variable damper 3620. An example of the use of Embodiment 8 as an artificial hip is provided in the next section.

Usage Example for Embodiment 8

Figure 7:
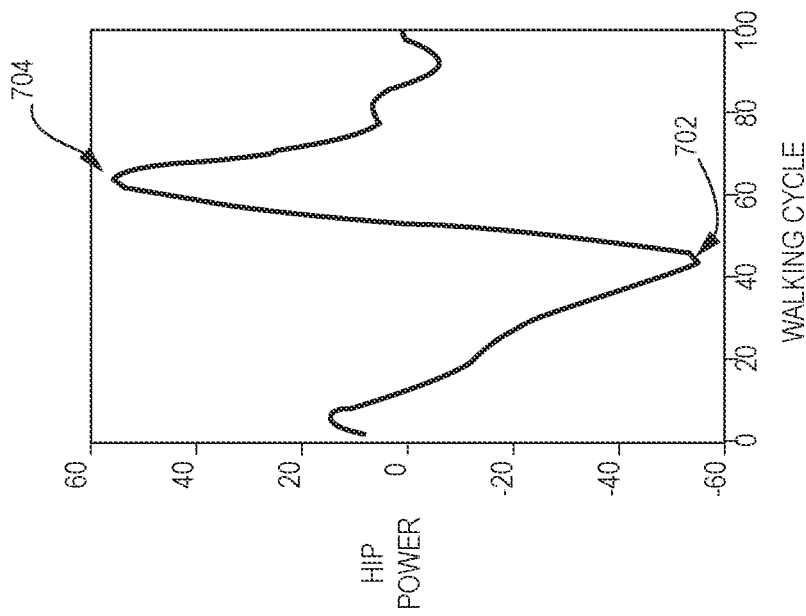
FIGS. 6 and 7 depict the phases of a walking cycle experienced by a human hip during level ground walking.
Figure 6:
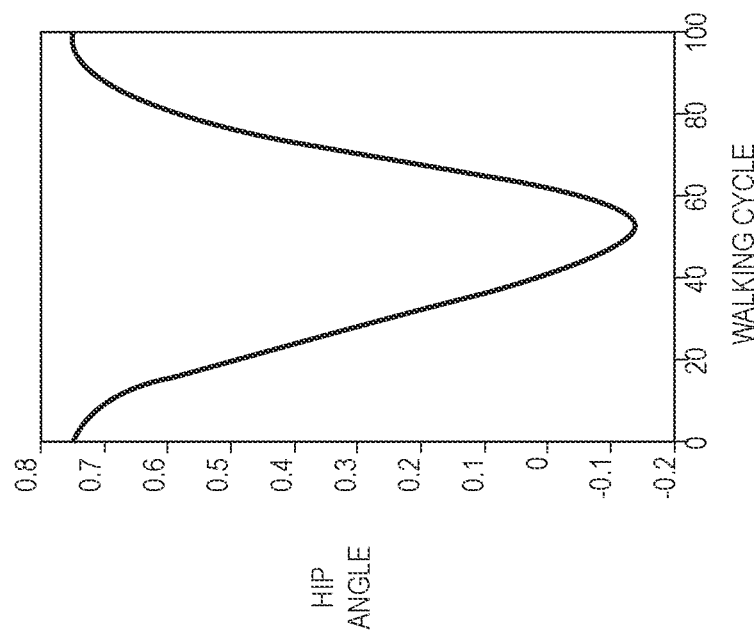

Basic hip biomechanics for level-ground walking, shown in FIGS. 6-7, can be modeled with a spring in parallel with a motor system. The Embodiment 8 hybrid architecture constitutes the least number of components to achieve basic hip functionality. During level-ground walking, the global variable damper 3620 outputs a large damping value such that the global damper flexion springs 3625 store elastic energy during terminal hip extension and release that stored energy during early hip flexion to promote knee flexion and toe-off throughout terminal stance. After this elastic energy is released, the global flexion springs 3640 and 3642 store energy throughout mid to terminal hip flexion and release that stored energy during early to mid hip extension to promote limb retraction and forward propulsion. To the extent to which the desired joint behavior deviates from a conservative spring response, the motor and global variable damper are controlled to generate or absorb mechanical power as needed.

In addition to the motor 3610, global variable damper 3620 and global damper springs 3625, the hybrid biomimetic hip actuator seen in FIGS. 34-36 also includes a two way global spring consisting of the passive flexion spring 3640 and the passive extension spring 3642. The approximate equilibrium position of this global spring assembly is such that the spring exerts little to no force when standing with an erect posture. This global spring is important for uphill locomotion when the hip actuator is used for an orthosis or exoskeleton. During the swing phase as the hip flexes and the foot is placed on the next foothold, the global spring stores energy and then that energy is released to augment hip extension as the body is lifted upwardly during the stance phase. By adjusting the stiffness and equilibrium position of the global spring, muscles that flex the hip during the swing phase will fatigue at the same time as muscles that extend the hip during stance. Since the work required to ascent a hill is better distributed across a greater muscle volume as a result of the global spring, muscle fatigue can be effectively delayed.

Embodiment 9

Mechanical Design

Figure 39:
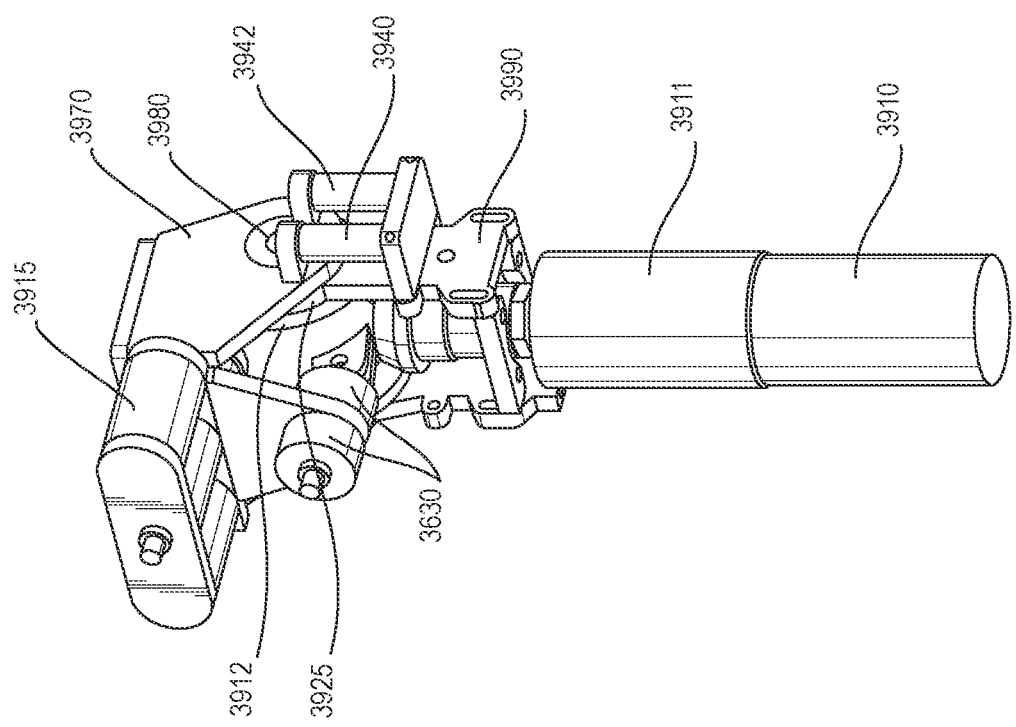
FIG. 39 is a perspective drawing illustrating the physical implementation of the ninth embodiment of the invention.
Figure 37:
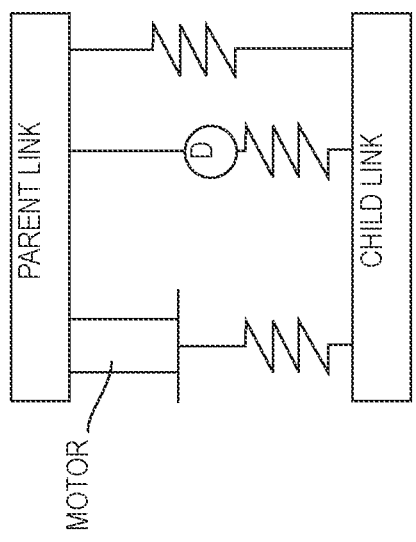
FIG. 37 is a lumped parameter model a ninth embodiment of the invention, a biomimetic hip.
Figure 38:
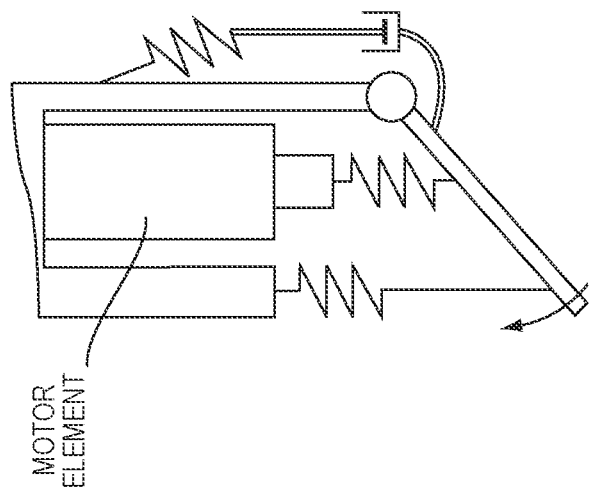
FIG. 38 is a schematic drawing of the ninth embodiment of the invention.

Embodiment 9 is a further biomimetic hybrid hip design seen in FIGS. 37-39. Five elements are included in the design as seen in FIG. 39: an electric motor 3910, a gearbox 3911, a bevel drive gear 3912, a motor series spring 3915 for joint flexion and extension, a global variable damper 3925, global series damper springs 3630, and a bi-directional global spring consisting of a passive flexion spring 3940 and a passive extension spring 3942. Additionally, global damper coil springs 3630 (Series Damper Springs) are included for joint flexion and extension. The global damper 3925 is a rotary magnetorheological (MR) variable-damper technology where MR fluid is used in the shear mode. The pelvis structure at 3970 supports the joint 3980 about which the thigh structure 3990 rotates.

In addition to the capabilities offered by Embodiment 2, Embodiment 9 allows for the engagement of the second series damper spring, the damper series spring 3630, at any time during system operation. Further, the amount of energy stored or released from the damper series spring can be modulated using the global variable damper. An example of the use of Embodiment 9 as an artificial hip is provided in the next section.

Usage Example for Embodiment 9

The functionality of the hybrid hip actuator corresponding to Embodiment 9 is similar to the Embodiment 8 hip system except that the addition of the motor series spring 3915 that allows the system to better able to augment the spring response from the global damper spring. Since the motor can perform a position control on the motor series spring, the force output from that spring can be effectively controlled, allowing for accurate modulation of impedance and motive force in parallel with the global variable damper/global damper spring components. Hence, the hip system of Embodiment 9 can more effectively absorb and generate mechanical power to augment the passive spring responses from the global damper spring and global two way spring.

Embodiment 10

Mechanical Design

Embodiment 10 comprises a motor 4910, a motor series spring 4913, a motor series damper 4915, a damper series spring at 4920, a motor parallel damper 4914, a gearbox 4922, a bevel gear 4923, a global damper 4916, and a global damper springs at 4918 and 4919. In addition to the capabilities offered by Embodiment 6, Embodiment 10 allows for the engagement of a second series spring, the damper series spring 4920, at any time during system operation. Further, the amount of energy stored or released from the damper series spring 4920 can be modulated using the global variable damper 4916. The pelvis structure at 4930 supports the joint axis 4945 about which the thigh structure 4950 rotates. An example of the use of Embodiment 10 as an artificial hip is provided in the next section.

Usage Example for Embodiment 10

Figure 42:
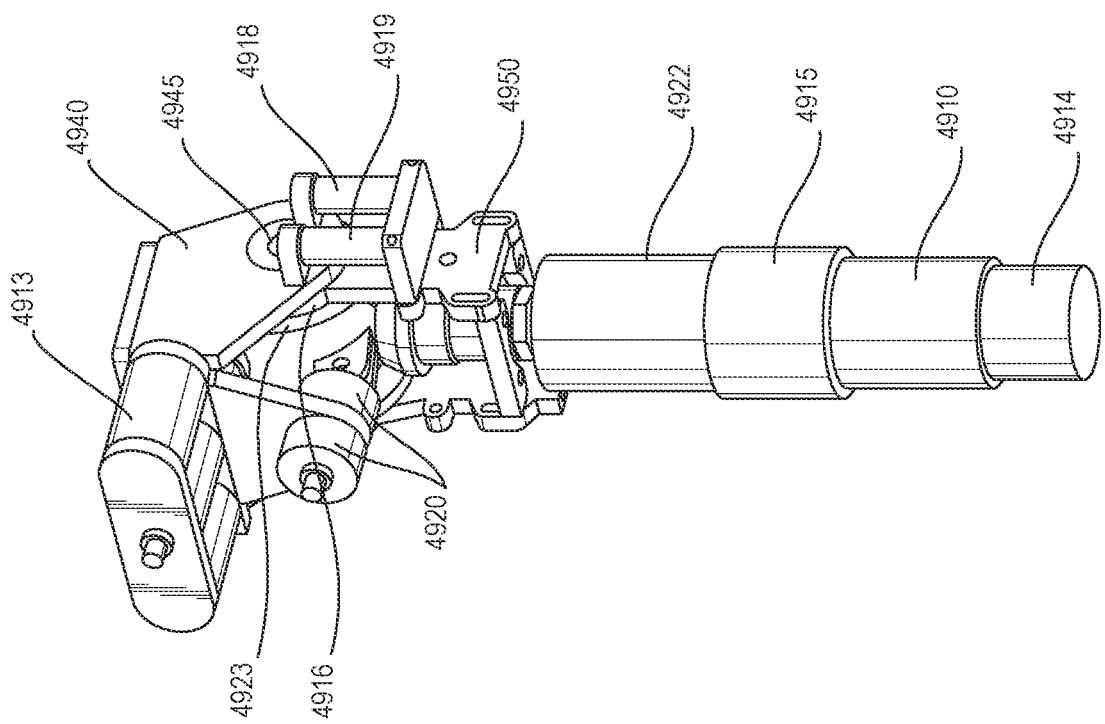
FIG. 42 is a perspective drawing illustrating the physical implementation of the tenth embodiment of the invention.
Figure 40:
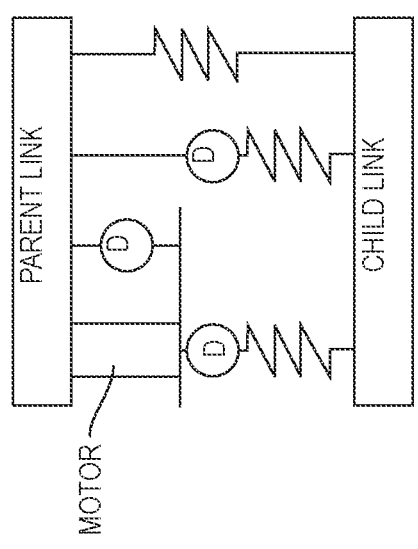
FIG. 40 is a lumped parameter model a tenth embodiment of the invention, a biomimetic ankle.
Figure 41:
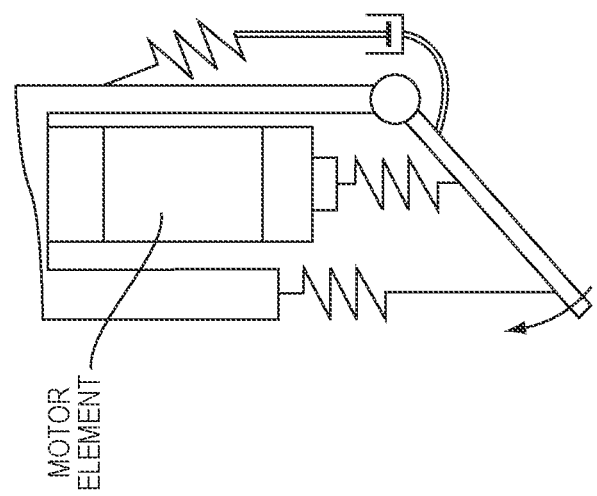
FIG. 41 is a schematic drawing of the tenth embodiment of the invention.
Figure 46:
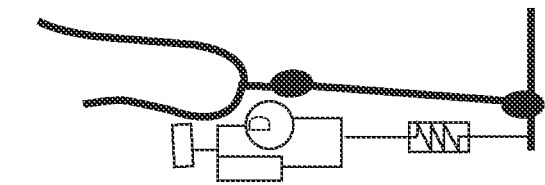
FIGS. 43-49 illustrates a Biomimetic Hybrid Actuator that spans both the knee and ankle joints.
Figure 45:
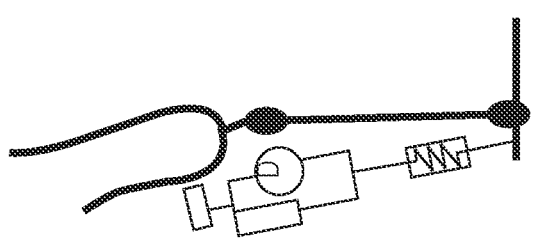
Figure 44:
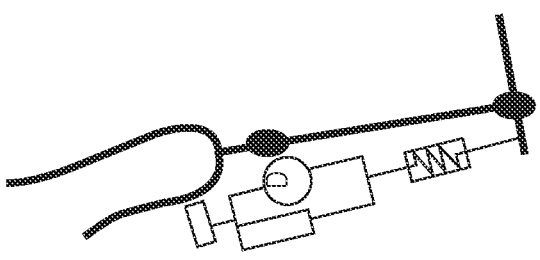

The mechanical design and the corresponding schematic for Embodiment 10, as used for an artificial hip application, are shown in FIGS. 42 and 41. The functionality of the hybrid hip actuator corresponding to Embodiment 10 is similar to the Embodiment 9 hip system except for the functional capabilities resulting from the addition of the motor series and parallel variable dampers 4915 and 4914 respectively. These added components offer several advantages to the hybrid hip actuator of Embodiment 9. The motor series variable damper 4915 allows the Embodiment 10 hip system to be back driven very easily for tasks where hybrid actuator force needs to be minimized at minimal energy demands from the power supply. The addition of the motor series variable damper 4915 allows the gearbox to freewheel at high angular rates without the need for the motor to slew as well, lowering the minimal force output of the biomimetic actuator at minimal power input requirements. In addition to improving the low-energy, minimum force capabilities of the actuator, the actuator of Embodiment 10 can dissipate mechanical energy without back driving the motor by once again using the motor parallel variable damper 4914 to lock the motor rotor at low energy demands from the power supply. Although controlling the actuator in this manner eliminates the opportunity to employ the motor as a generator, it is beneficial in that it will result in a quieter biomimetic hip operation.

Poly-Articular Actuation Using Biomimetic Hybrid Actuators

In the previous sections, ten Biomimetic Hybrid Actuators were described and specific examples were provided as to their use for ankle, knee and hip actuation. For each of these descriptions, the hybrid actuator spanned a single joint. In this section, a Biomimetic Hybrid Actuator that spans more than one rotary joint is describe in connection with FIGS. 43-49 of the drawings. The functional purpose of poly-articular muscle architectures in the human leg is to promote the transfer of mechanical energy from proximal muscular work to distal joint power generation {10}. To capture truly biomimetic limb function, both muscle-like actuators and mono, bi, and poly-articular artificial musculoskeletal architectures are critical. Hence, in this section we describe the use of Biomimetic Hybrid Actuators across two or more rotary joints.

As a particular demonstration of Biomimetic Hybrid Actuator usage across more than one rotary joint, we describe the use of the Embodiment 3 actuator (see FIGS. 19-21) as an artificial Gastrocnemius muscle that spans both knee and ankle artificial rotary joints. In FIGS. 43-49, seven leg postures are shown, depicting the movement of a normal human ankle joint 4302 and knee joint 4304 (joining the shin member 4305) during the stance period of level-ground walking A bi-articular Biomimetic Hybrid Actuator is attached posteriorly to the artificial leg, spanning ankle and knee joints. Here the child link corresponds to the artificial foot 4310, and parent link 4303 corresponds to the artificial thigh or femur section of the biomimetic limb. The Embodiment 3 actuator, comprising motor, motor series spring and motor parallel variable damper, attaches between these two locations, and therefore acts in a bi-articular manner.

Figure 1:
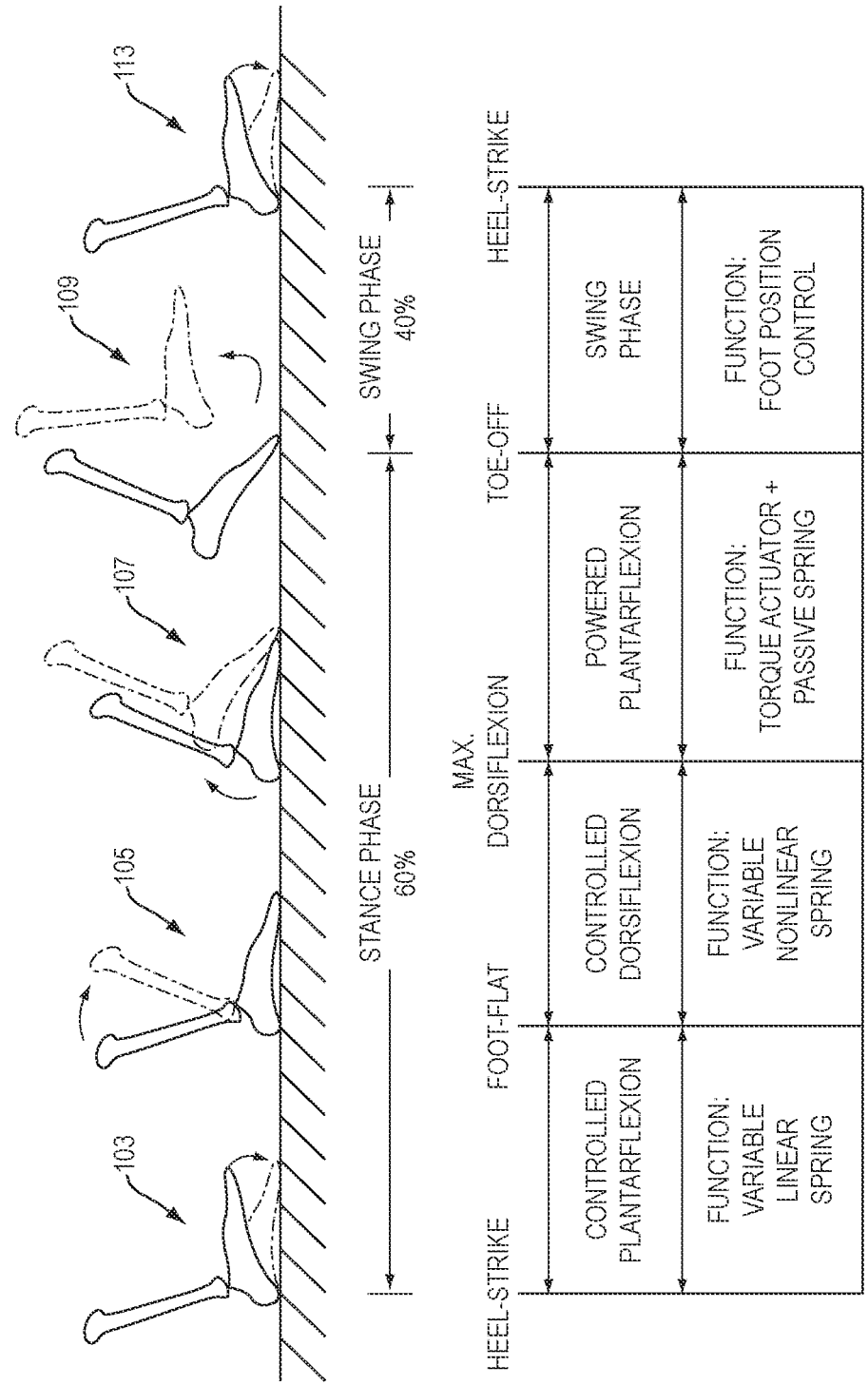
FIG. 1 illustrates the different phases of a walking cycle experienced by a human ankle and foot during level ground walking.
Figure 2:
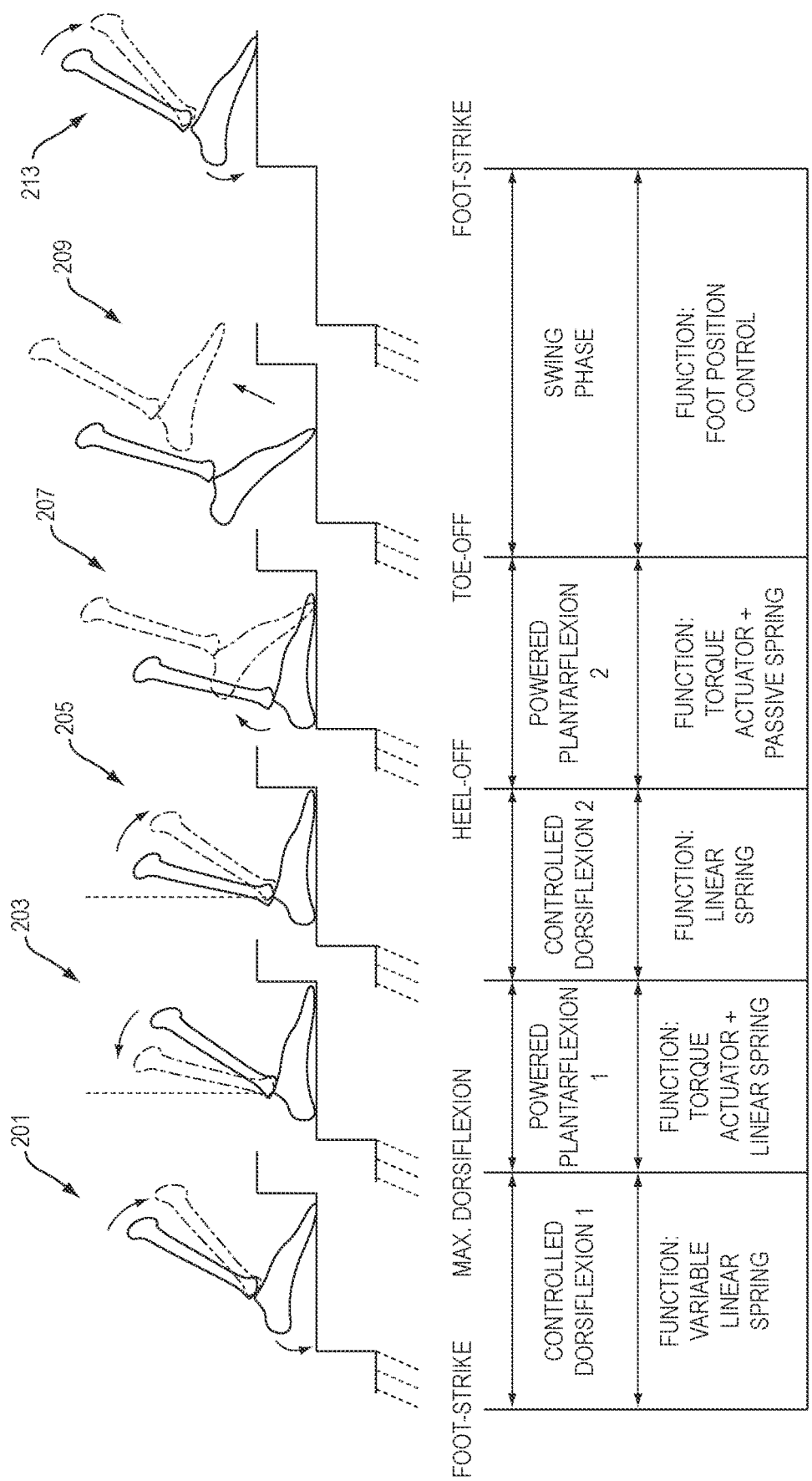
FIG. 2 depicts the phases of a walking cycle experienced by a human ankle and foot when ascending stairs.
Figure 3:
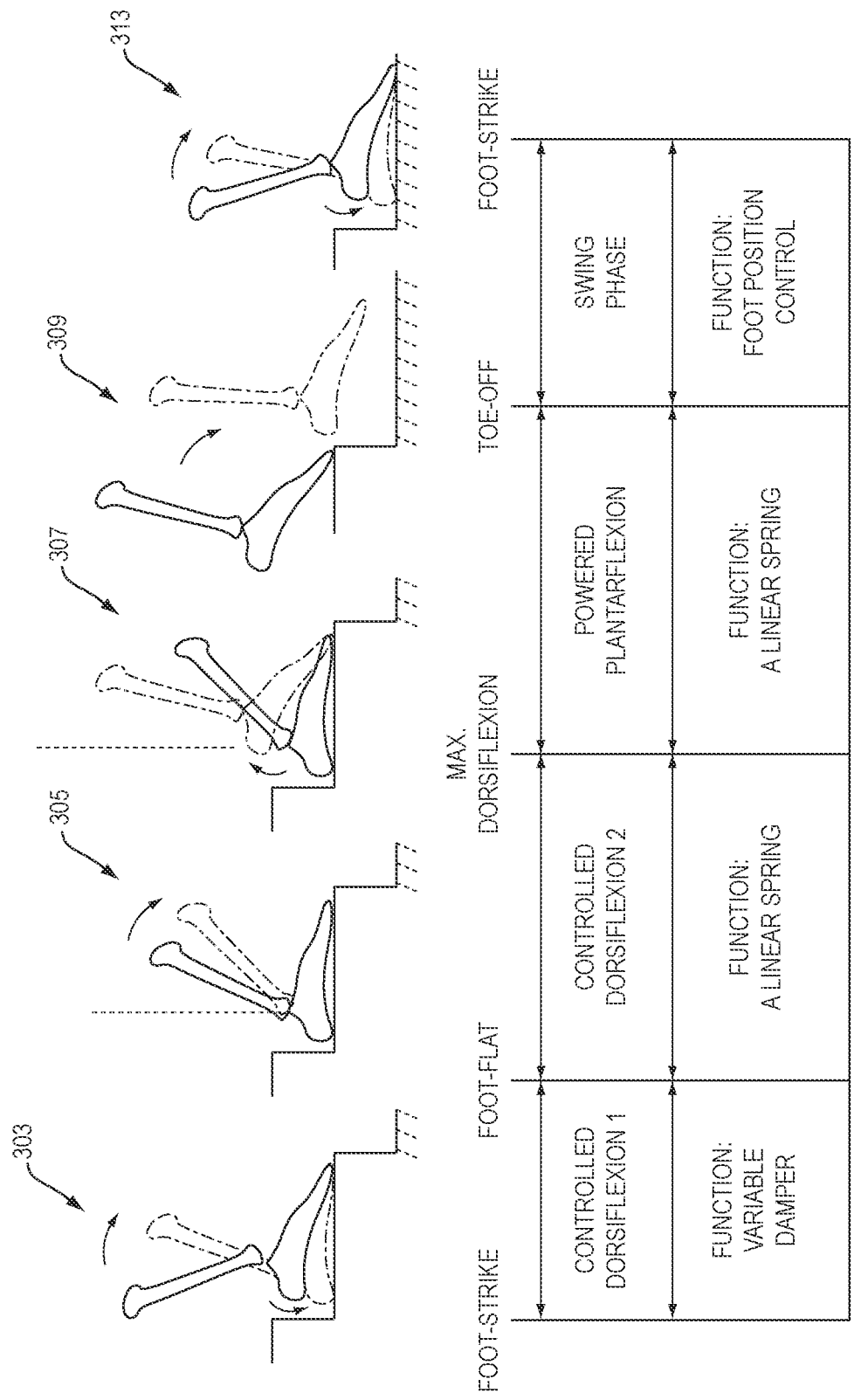
FIG. 3 depicts the phases of a walking cycle experienced by a human ankle and foot during stair descent.
Figure 4:
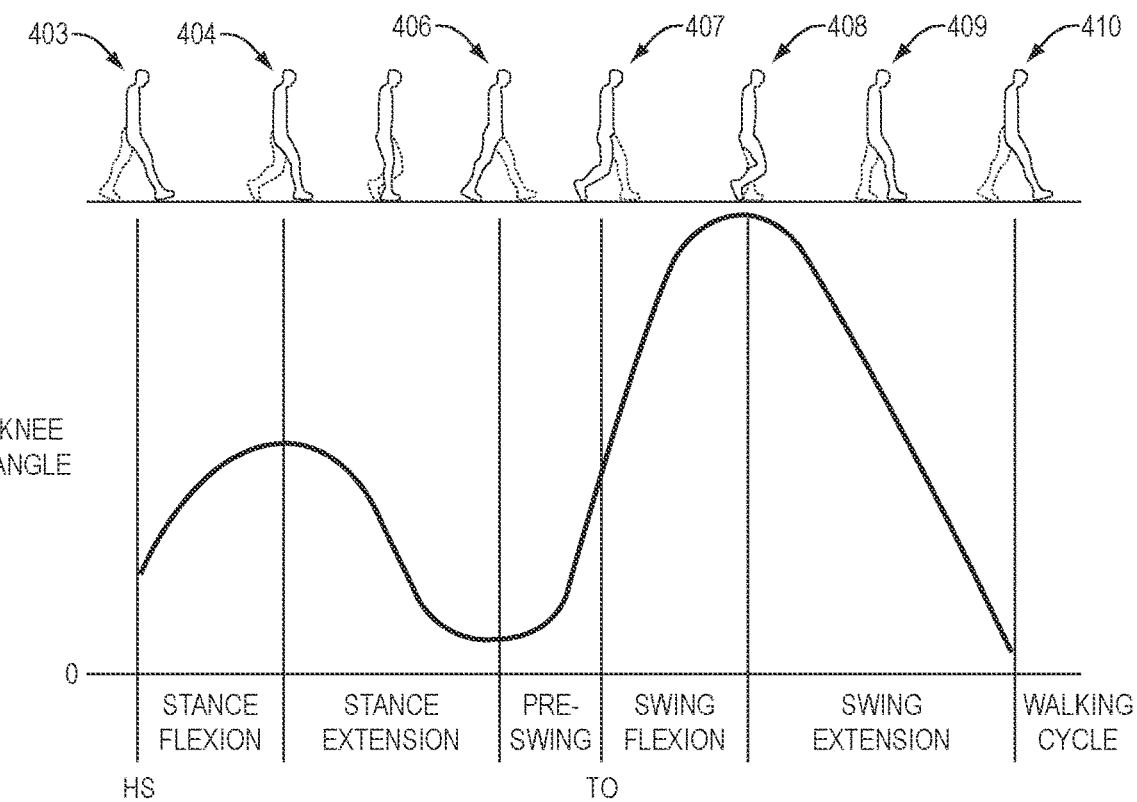
FIGS. 4 and 5 depicts the phases of a walking cycle experienced by a human knee when walking on level ground.
Figure 43:
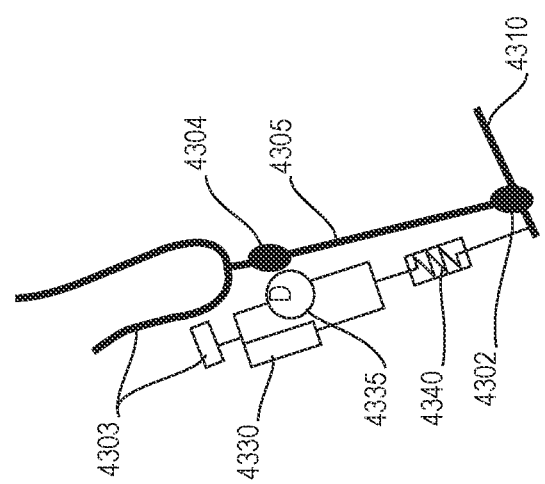
Figure 49:
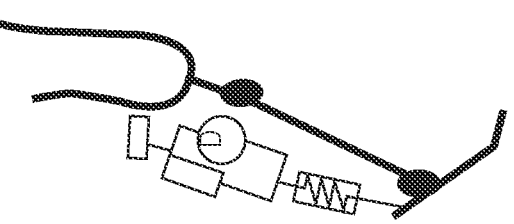
Figure 48:
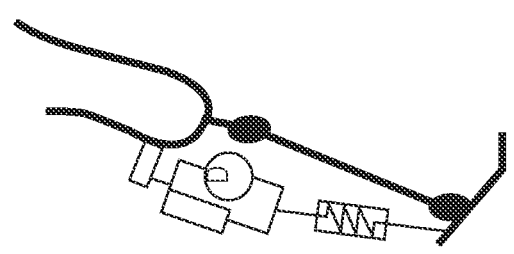
Figure 47:
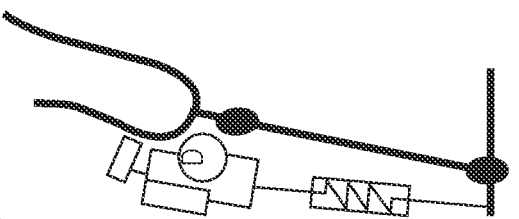

The functionality of the Embodiment 3 system as a bi-articular actuator is described for level-ground walking using the leg postures sketched in FIGS. 43-49. Although we give only one example here, it should be understood that any of the ten hybrid actuator embodiments could be employed in a poly-articular manner where the hybrid actuator spans more than one rotary joint. During ankle controlled plantar flexion and knee early stance flexion (leg postures seen in FIGS. 43-45), both the human ankle and knee exhibit a spring-like behavior where joint torque is a function of joint angular position. This spring-like behavior begins at approximately 5% gait cycle after the knee has begun flexing during early stance (see FIGS. 4-5). In the artificial biomimetic leg design of FIGS. 43-49, immediately following heel strike as seen in FIG. 43 the motor 4330 and motor parallel variable damper 4335 are controlled to absorb mechanical energy in a controlled manner. For this control behavior, the variable damper dissipates mechanical energy as heat, and the motor acts as a generator. After this initial period of about five degrees of knee flexion (mid flexion phase) the variable damper then outputs a much higher damping value such that elastic energy is stored in the motor series compression springs 4340. Here the series compression springs are tuned to have a maximal stiffness required for this period of gait. To achieve lower effective stiffnesses from mid to terminal knee flexion, the motor and motor parallel variable damper absorbs mechanical energy as the motor series compression springs are compressed. Here again, for this control behavior, the variable damper dissipates mechanical energy as heat, and the motor acts as a generator.

During ankle controlled dorsiflexion and knee stance extension (leg postures seen in FIGS. 45 to 47), both the human ankle and knee exhibit a spring-like behavior where joint torque correlates with joint angular position. However, as walking speed increases, ankle stiffness during controlled dorsiflexion increases. In addition, as speed increases the ankle torque versus angle curve becomes increasingly non-linear characterized by a hardening behavior where ankle torque increases with increasing angular deflection. It is also the case in walking that peak knee flexion becomes more pronounced with increasing walking speed, increasing the opportunity for energy to be transferred from hip muscular power exertion to ankle power generation. In the case of the bi-articular Biomimetic Hybrid Actuator shown in FIGS. 43-49, the elastic energy stored during mid to terminal early stance knee flexion/controlled is then released during early to mid knee extension. This positive power output corresponds to 502 in FIG. 5. After the elastic energy (leg postures seen in FIGS. 43-45) is released, the motor series tension springs 4340 then begin to compress, storing energy from mid to terminal knee extension. Here the series tension springs are tuned to correspond to the minimal stiffness, slow walking human ankle stiffness value. To achieve higher stiffnesses as walking speed increases, the motor does work on the spring, slowly storing energy throughout the controlled dorsiflexion/terminal knee extension period, resulting in an ankle joint profile with increasing torque with increasing angular deflection.

Throughout terminal stance (leg postures seen in FIGS. 47-49), the human ankle undergoes powered plantar flexion, and the human knee begins rapid flexion in preparation for the swing phase. During this period of gait, the human ankle's positive power generation is quite large in comparison with the human knee's positive power generation (See 503, FIG. 5), especially at fast walking speeds. To achieve these joint powers, the energy stored in the motor series tension springs during controlled dorsiflexion/knee extension is released, causing the knee to flex and the ankle to plantar flex. This positive power release at the knee corresponds to power output 502 in FIG. 5. To achieve a relatively higher power output through the ankle compared to the knee, the effective moment arm of the ankle joint could be significantly larger than that for the knee. During the swing phase, the motor, motor parallel variable damper and motor series springs are used to absorb and generate mechanical power as needed to reproduce a human-like swing phase trajectory.

It should be understood that the bi-articular hybrid actuator described herein could be used in a variety of ways. For example, mono-articular motor, spring and/or damper components could act about the biomimetic ankle and/or knee joints to supplement the mechanical output resulting from the bi-articular hybrid actuator of FIG. 17. Still further, any of the ten embodiments described herein could be employed as part of an artificial musculoskeletal architecture comprising mono and poly-articular actuation strategies.

Sensing and Control

Figure 50:
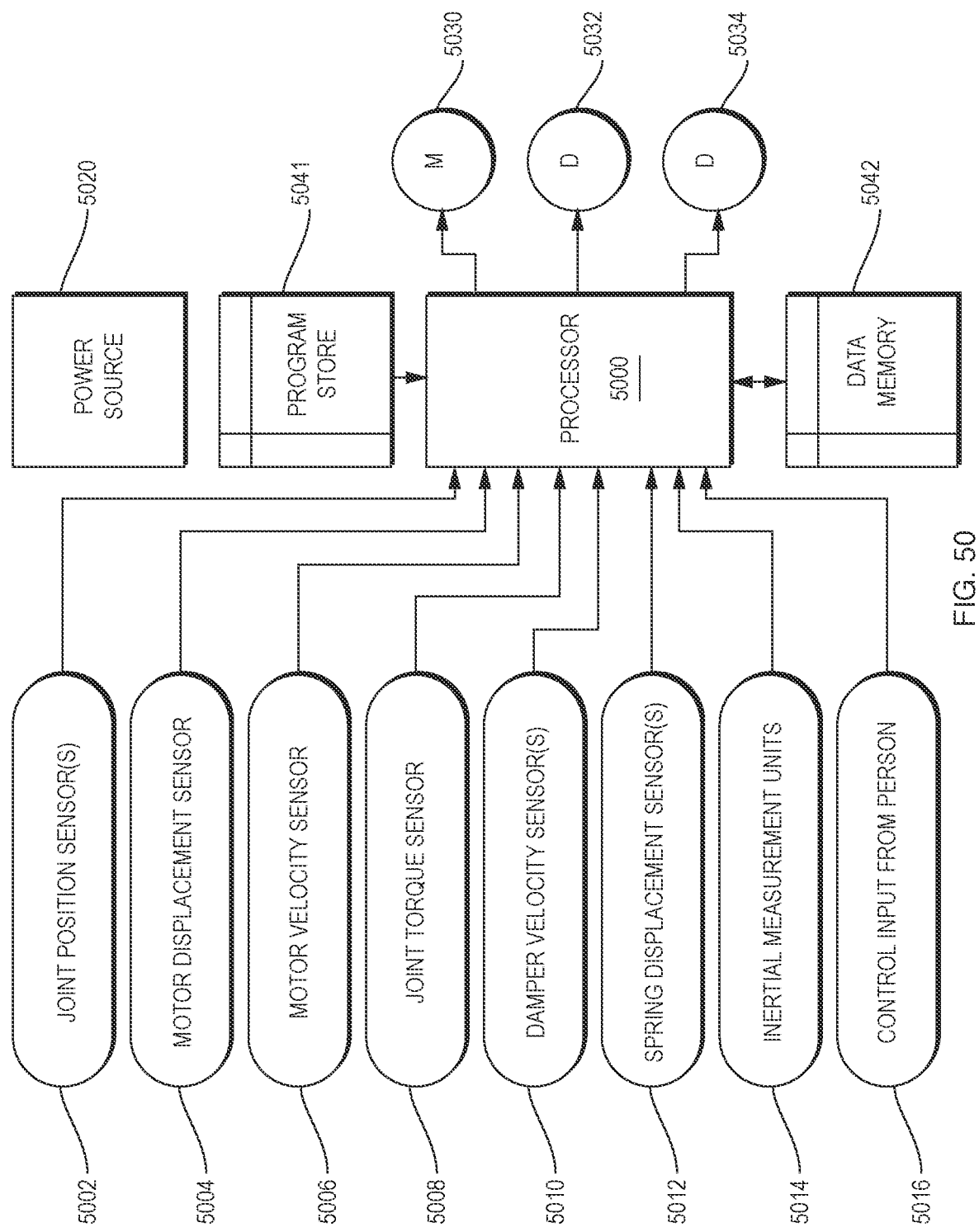
FIG. 50 is a schematic block diagram of a sensing and control mechanism used to control the operation of the motors and dampers in a Biomimetic Hybrid Actuator.

As described above in connection with FIGS. 1-7, investigations of the biomechanics of human limbs have revealed the functions performed by the ankle, knee and hip joints during normal walking over level ground, and when ascending or descending a slope or stairs. As discussed above, these functions may be performed in an artificial joint or limb using motors to act as torque actuators and to position the skeletal members during a specific times of walking cycle, using springs in combination with controllable dampers to act as linear springs and provide controllable damping at other times in the walking cycle. The timing of these different functions occurs during the walking cycle at times described in detail above in connection with FIGS. 1-7 of the drawings. The specific mechanical structures, that is the combinations of motors, springs and controllable dampers used in the embodiments depicted in FIGS. 8-49 and described above are specifically adapted to perform the functions needed by specific joint and limb structures. A variety of techniques may be employed to automatically control the motor and controllable dampers at the times needed to perform the functions illustrated in FIGS. 1-7 and any suitable control mechanism may be employed. FIG. 50 depicts the general form of a typical control mechanism in which a multiple sensors are employed to determine the dynamic status of the skeletal structure and the components of the hybrid actuator and deliver data indicative of that status to a processor seen at 5000 which produces control outputs to operate the motor actuator and to control the variable dampers.

The sensors used to enable general actuator operation and control can include:

(1) Position sensors seen at 5002 in FIG. 50 located at the biomimetic joint axis to measure joint angle (a rotary potentiometer), and at the motor rotor to measure total displacement of the motor's drive shaft (as indicated at 5004) and additionally the motor's velocity (as indicated at 5006). A single shaft encoder may be employed to sense instantaneous position, from which motor displacement and velocity may be calculated by the processor 5000.

(2) A force sensor (strain gauges) to measure the actual torque borne by the joint as indicated at 5008.

(3) Velocity sensors on each of the dampers (rotary encoders) as indicated at 5010 in order to get a true reading of damper velocity.

(4) A displacement sensor on each spring (motor series spring and global damper spring) as indicated at 5012 in order to measure the amount of energy stored.

(5) One or more Inertial Measurement Units (IMUs) seen at 5014 which can take the form of accelerometers positioned on skeletal members from which the processor 5000 can compute absolute orientations and displacements of the artificial joint system. For example, the IMU may sense the occurrence of events during the walking cycle such as heel strike and toe-off seen in FIGS. 1-3.

(6) One or more control inputs manipulatable by a person, such a wearer of a prosthetic joint or the operator of a robotic system, to control such things as walking speed, terrain changes, etc.

The processor 5000 preferably comprises a microprocessor which is carried on the body and typically operated from the same battery power source 5020 used to power the motor 5030 and the controllable dampers 5032 and 5034. A nonvolatile program memory 5041 stores the executable programs that control the processing of the data from the sensors and input controls to produce the timed control signals which govern the operation of the actuator motor and the dampers. An additional data memory seen at 5042 may be used to supplement the available random access memory in the microprocessor 5000.

Instead of directly measuring the deflection of the motor series springs as noted at (4) above, sensory information from the position sensors (1) can be employed. By subtracting the biomimetic joint angle from the motor output shaft angle, it is possible to calculate the amount of energy stored in the motor series spring. Also, the motor series spring displacement sensor can be used to measure the torque borne by the joint because joint torque can be calculated from the motor series output force.

Many variations exist in the particular sensing methodologies employed in the measurement of the listed parameters. Although this specification describes preferred sensing methods, each has the goal of determining the energy state of the spring elements, the velocities of interior points, and the absolute movement pattern of the biomimetic joint itself.

REFERENCES

The following published materials provide background information relating to the invention. Individual items are cited above by using the reference numerals which appear below and in the citations in curly brackets.

{1} Palmer, Michael. Sagittal Plane Characterization of Normal Human Ankle Function across a Range of Walking Gait Speeds. Massachusetts Institute of Technology Master's Thesis, 2002.

{2} Gates Deanna H., Characterizing ankle function during stair ascent, descent, and level walking for ankle prosthesis and orthosis design. Master thesis, Boston University, 2004.

{3} Hansen, A., Childress, D. Miff, S. Gard, S. and Mesplay, K., The human ankle during walking: implication for the design of biomimetric ankle prosthesis, Journal of Biomechanics (In Press).

{4} Koganezawa, K. and Kato, I., Control aspects of artificial leg, IFAC Control Aspects of Biomedical Engineering, 1987, pp. 71-85.

{5} Herr H, Wilkenfeld A. User-Adaptive Control of a Magnetorheological Prosthetic Knee. Industrial Robot: An International Journal 2003; 30: 42-55.

{6} Seymour Ron, Prosthetics and Orthotics: Lower limb and Spinal, Lippincott Williams & Wilkins, 2002.

{7} G. A. Pratt and M. M. Williamson, "Series Elastic Actuators," presented at 1995 IEEE/RSJ International Conference on Intelligent Robots and Systems, Pittsburgh, Pa.

{8} Inman V T, Ralston H J, Todd F. Human walking Baltimore: Williams and Wilkins; 1981.

{9} Hof. A. L. Geelen B. A., and Berg, Jw. Van den, "Calf muscle moment, work and efficiency in level walking; role of series elasticity," Journal of Biomechanics, Vol 16, No. 7, pp. 523-537, 1983.

{10} Gregoire, L., and et al, Role of mono- and bi-articular muscles in explosive movements, International Journal of Sports Medicine 5, 614-630.

What is claimed is:

1. A device comprising:
a mechanical joint;
an actuator comprising:
a motor adapted to impart a torque on the joint;
a spring coupled in series with the motor; and
a variable damper or clutch coupled parallel to the motor, wherein the variable damper or clutch is a motor-parallel variable damper or clutch, coupled parallel to the motor and not to the spring coupled in series with the motor;
a sensory system comprising at least one sensor selected from the group consisting of a position sensor, a force sensor, and a velocity sensor; and
a processor connected to the actuator and the sensory system for outputting control signals to control operation of the actuator;
wherein the processor outputs control signals that modulate damping or clutching by the variable damper or clutch to cause the spring coupled in series with the motor to store energy during a portion of a gait cycle and release the stored energy in another portion of the gait cycle.

2. The device of claim 1, wherein the device includes a mechanical knee joint.

3. The device of claim 2, wherein the portion of the gait cycle is stance knee flexion and the another portion of the gait cycle is stance knee extension.

4. The device of claim 1, wherein the device includes a mechanical knee joint, and wherein the motor-parallel damping or clutching occurs during stance extension of the gait cycle to store the energy in the spring for later release of the energy during early pre-swing.

5. The device of claim 1, wherein the device includes a mechanical knee joint and wherein the damping or clutching occurs during swing flexion to store the energy for later release of the energy during swing extension.

6. The device of claim 1, wherein the device includes a mechanical hip joint.

7. The device of claim 6, wherein the portion of the gait cycle is terminal hip extension, and the another portion of the gait cycle is active hip flexion.

8. A device comprising:
- at least one of a mechanical knee joint and a mechanical hip joint;
- an actuator comprising:
  - a motor adapted to impart a torque on the joint;
  - a spring coupled in series with the motor; and
  - a variable damper or clutch coupled parallel to the motor, wherein the variable damper or clutch is a motor-parallel variable damper or clutch, coupled parallel to the motor and not to the spring coupled in series with the motor;
- a sensory system comprising at least one sensor selected from the group consisting of a position sensor, a force sensor, and a velocity sensor; and
- a processor connected to the actuator and the sensory system for outputting control signals to control operation of the actuator;
- wherein the processor outputs control signals that modulate damping or clutching by the variable damper or clutch to cause the spring coupled in series with the motor to store energy by flexion of the joint in the case of the mechanical knee joint, and extension of the joint in the case of the mechanical hip joint, during a portion of a gait cycle and release the stored energy in another portion of the gait cycle.

9. The device of claim 8, wherein the spring coupled in series with the motor releases the stored energy in the another portion of the gait cycle by extension in the case of the mechanical knee joint and by flexion in the case of the mechanical hip joint.

10. The device of claim 9, wherein the portion of the gait cycle is terminal hip extension, and the another portion of the gait cycle is active hip flexion.

11. The device of claim 8, wherein the device includes the mechanical knee joint.

12. The device of claim 9, wherein the portion of the gait cycle is stance knee flexion and the another portion of the gait cycle is stance knee extension.

13. The device of claim 8, wherein the device includes the mechanical knee joint, and wherein the motor-parallel damping or clutching occurs during stance extension of the gait cycle to store the energy in the spring for later release of the energy during early pre-swing.

14. The device of claim 8, wherein the device includes the mechanical knee joint and wherein the damping or clutching occurs during swing flexion to store the energy for later release of the energy during swing extension.

15. The device of claim 8, wherein the device includes the mechanical hip joint.

* * * * *